US009220672B2

(12) United States Patent
Lang

(10) Patent No.: US 9,220,672 B2
(45) Date of Patent: Dec. 29, 2015

(54) PEPTIDE FOR USE IN THE TREATMENT OF SKIN CONDITIONS

(75) Inventor: Christine Lang, Berlin (DE)

(73) Assignee: ORGANOBALANCE GMBH, Berlin (DE)

( * ) Notice: Subject to any disclaimer, the term of this patent is extended or adjusted under 35 U.S.C. 154(b) by 0 days.

(21) Appl. No.: 13/984,120

(22) PCT Filed: Feb. 3, 2012

(86) PCT No.: PCT/EP2012/000697
§ 371 (c)(1),
(2), (4) Date: Oct. 15, 2013

(87) PCT Pub. No.: WO2012/107244
PCT Pub. Date: Aug. 16, 2012

(65) Prior Publication Data
US 2014/0057850 A1    Feb. 27, 2014

(30) Foreign Application Priority Data
Feb. 9, 2011  (EP) .................................. 11153771

(51) Int. Cl.
| | | |
|---|---|---|
| *A61K 38/07* | (2006.01) | |
| *C07K 5/037* | (2006.01) | |
| *A61Q 19/00* | (2006.01) | |
| *A61K 8/64* | (2006.01) | |
| *C07K 5/02* | (2006.01) | |
| *C07K 5/09* | (2006.01) | |
| *A61K 38/00* | (2006.01) | |
| *A61Q 5/02* | (2006.01) | |
| *A61Q 19/10* | (2006.01) | |

(52) U.S. Cl.
CPC ................ *A61K 8/64* (2013.01); *A61Q 19/007* (2013.01); *C07K 5/0215* (2013.01); *C07K 5/0815* (2013.01); *A61K 38/00* (2013.01); *A61Q 5/02* (2013.01); *A61Q 19/10* (2013.01)

(58) Field of Classification Search
CPC ....... A61K 8/64; A61K 38/00; C07K 5/0215; C07K 5/0815; A61Q 5/02; A61Q 19/007; A61Q 19/10
See application file for complete search history.

(56) References Cited

U.S. PATENT DOCUMENTS 7,056,942 B2 *  6/2006  Hildesheim et al. .......... 514/411

FOREIGN PATENT DOCUMENTS

| EP | 1997826 | 12/2008 |
|---|---|---|
| GB | 1523812 | 9/1978 |
| WO | 01/09173 | 2/2001 |
| WO | 2005/048968 A1 | 6/2005 |
| WO | 2006/136420 A2 | 12/2006 |

OTHER PUBLICATIONS

Definition of derivative, from http://cancerweb.ncl.ac.uk/cgi-bin/omd?query=derivative, pp. 1-5, accessed Jul. 7, 2005.*
Definition of moiety, from http://dictionary.reference.com/browse/moiety, pp. 1-3. Accessed Aug. 26, 2010.*
Water, from http://www.biology-online.org/dictionary/Water, pp. 1-3, accessed Apr. 24, 2014.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Vippagunta et al, Crystalline solids, Advanced Drug Delivery Reviews, 2001, 48, pp. 3-26.*
Magnet et al, Specificity of L,D-Transpeptidases from Gram-positive Bacteria Producing Different Peptidoglycan Chemotypes, The Journal of Biological Chemistry, 2007, 282, pp. 13151-13159.*
Types of Inflammation, from http://quizlet.com/5801283/types-of-inflammation-flash-cards/alphabetical, pp. 1-2, accessed Nov. 5, 2014.*
Dermatitis-Symptoms diagnosis and treatment, from http://www.webmd.boots.com/skin-problems-and-treatments/guide/dermatitis?print=true, pp. 1-3, accessed Nov. 5, 2014.*
What is inflammation and What causes inflammation, from http://www.medicalnewstoday.com/articles/248423.php, pp. 1-14, accessed Nov. 5, 2014.*
Bobrova et al., "Synthesis and biological activity of branched enkephal in analogues", European Journal of Medicine Cheistry, Editions Scientifique Elsevier, Paris, FR, vol. 33, No. 4, Apr. 1, 1998, pp. 255-266.
Rollan et al., International Journal of Food Microbiology 70 2001. 303-307.
Matsuquchi et aI.,Clinical and Diagnostic Laboratory Immunology, Mar. 2003, p. 259-266 vol. 10, No. 2.
Stentz et al., Applied and Environmental Microbiology, Oct. 2000, p. 4272-4278 vol. 66, No. 10.
Varmanen et al., Journal of Bacteriology, Jan. 2000, p. 146-154 vol. 182, No. 1 in J. Bacteriology 182 (2000), 146-154.

* cited by examiner

*Primary Examiner* — Julie Ha
*Assistant Examiner* — Li Ni Komatsu
(74) *Attorney, Agent, or Firm* — Ann Wieczorek; Mayer & Williams PC

(57) ABSTRACT

The present invention relates to a peptide of the following formula (I) $X_1(X_2)$-$X_3$-$X_4$ or a salt or solvate thereof, wherein is an amino acid comprising two or more NH-functionalities, and $X_2$, $X_3$, and $X_4$ are, independently from one another, an amino acid residue, and wherein the salt or solvate is preferably a physiologically acceptable salt or solvate.

33 Claims, 3 Drawing Sheets

PEPTIDE FOR USE IN THE TREATMENT OF SKIN CONDITIONS

CROSS REFERENCE TO RELATED APPLICATIONS

This application is a 371 of International Application No. PCT/EP12/00697, filed Feb. 3, 2012 which claims benefit and priority to European Application No. 11153771.8, filed Feb. 9, 2011 herein incorporated by reference in their entirety.

TECHNICAL FIELD

The present invention relates to a peptide and to compositions comprising a peptide, and to their respective non-therapeutic use in skin care. Furthermore the present invention relates to an anti-inflammatory drug, in particular for use in the treatment and prophylaxis of inflammation of epithelial tissues.

BACKGROUND OF THE INVENTION

The human skin is populated by a large variety of microorganisms that mainly live as commensals in a relatively stable composition on the surface of the skin. This normal skin flora is termed "resident skin flora" and supports the healthy appearance of the skin, which is shiny and sufficiently moist. In addition to creating a natural barrier for retaining moisture within the epidermis, the normal skin flora protects the skin against the intrusion of potentially pathogenic microorganisms.

Among the microorganisms constituting the resident microbial flora of healthy skin, often more than ninety percent thereof are *Staphylococcus epidermidis* (coagulase negative), *Micrococcus* spec., Diphteroids and propionibacteria. A typical imbalance of the skin microflora is for example observed when *Staphylococcus aureus* populates the skin microflora to an increasing extent, as a result of which the skin is increasingly prone to dryness. In this condition, the epidermis displays cracks and tends to show red areas as a result of inflammation. The danger of colonization by pathogenic microorganisms increases drastically in the case of small lesions or other damages on the surface of the skin, especially when the normal skin flora is diminished as a result of frequent washing, make-up, UV-light, or by antibiotics.

Thus, the microbial skin flora affects several factors of the skin that are of cosmetic relevance, namely the pH value of the skin, the barrier function and the skin's lipid content. In this respect, *S. epidermidis* assists the skin in fighting against pathogenic microorganisms by lowering the pH to values at which pathogens are not able to effectively grow. The water barrier function and the lipid content of the skin, on the other hand, depend on the ceramide content of the horny layers. Lowering of the ceramide content leads to a dried out and cracked skin condition. In this respect, a study conducted on atopical dermatitis patients having such a skin condition revealed that *Staphylococcus aureus* may dominate the microbial skin flora under these circumstances. In particular, it was found that as opposed to normal commensals of the skin, this pathogen displays a very high ceramidase activity. Under these conditions, the loss of humidity and lipids leads to the generation of inflammation of the epidermis.

WO 2006/136420 A2 relates to microorganisms, and in particular to microorganisms belonging to the genus *Lactobacillus*, which are able to stimulate the growth of one or more microorganisms of the resident skin microbial flora and which does not stimulate the growth of microorganisms of the transient pathogenic micro flora, as well as to the use of such microorganisms in cosmetic and pharmaceutical compositions, in particular for the treatment of dermatitis.

There however remains the need for a compound or composition which does not depend on cell cultures requiring special care and handling, and which are thus limited with respect to their application. In particular, the need exists for a compound or composition which may be easily produced in a cost-effective manner. Furthermore there is a need for a compound or composition which displays a low effective dose with respect to its beneficial effects, not only in view of providing more cost-effective cosmetic formulation, but also for opening new perspectives with respect to new applications in the field of both cosmetics and pharmaceuticals.

SUMMARY OF THE INVENTION

The present invention concerns a peptide of the following formula (I)

$$X_1(X_2)\text{-}X_3\text{-}X_4 \qquad (I)$$

or a salt or solvate thereof, wherein $X_1$ is an amino acid comprising two or more NH-functionalities, and $X_2$, $X_3$, and $X_4$ are, independently from one another, an amino acid residue, and wherein the salt or solvate is preferably a physiologically acceptable salt or solvate.

Furthermore, the present invention relates to a peptide according to the present invention as a medicament, and preferably as an anti-inflammatory drug. Furthermore, the present invention equally relates to a method for treating of a pro-inflammatory condition or disease in a subject, said method comprising administering to a subject suffering from the aforementioned condition or disease a therapeutically effective dose of the peptide of the invention, wherein the condition or disease being treated is preferably an inflammation of epithelial tissues, allergies, allergic reactions, rash, and/or rheumatoid arthritis, more preferably inflammation, allergies, and/or allergic reactions of the epidermis, more preferably dermatitis, and even more preferably atopic dermatitis, seborrhoeic dermatitis, psoriasis, poison-ivy dermatitis, eczema herpeticum, kerion, diaper rash, or scabies. In addition to this, the present invention also relates to a method for prophylaxis of a pro-inflammatory condition or disease in a subject, said method comprising administering to an apparently healthy subject a prophylactically effective dose of the peptide of the invention, wherein the method of prophylaxis of a pro-inflammatory condition or disease in a subject preferably involves the prophylaxis of inflammation of epithelial tissues, allergies, allergic reactions, rash, and/or rheumatoid arthritis, more preferably inflammation, allergies, and/or allergic reactions of the epidermis, more preferably dermatitis, and even more preferably atopic dermatitis, seborrhoeic dermatitis, psoriasis, poison-ivy dermatitis, eczema herpeticum, kerion, diaper rash, or scabies.

In addition to these, the present invention concerns both a cosmetic composition and a pharmaceutical composition, said compositions respectively comprising the peptide according to the present invention.

The present invention also concerns the use of the inventive peptide or of a composition of the invention for non-therapeutic skin care, preferably for the treatment and/or prophylaxis of dry skin condition. In addition to this, the present invention equally relates to a method of using the inventive peptide or of a composition of the invention for non-therapeutic skin care, preferably for the treatment and/or prophylaxis of dry skin condition, preferably dry facial skin and/or dry scalp, and even more preferably dry facial skin, said method comprising administering to a subject a cosmetically effective dose of the peptide of the invention.

Furthermore, the present invention preferably relates to the use of the inventive peptide or compositions for stimulating the growth of healthy normal resident skin microflora, preferably for stimulating the growth of healthy normal resident skin microflora belonging to the *Staphylococcus* genus. In addition to this the present invention equally relates to a method of using the inventive peptide or compositions for stimulating the growth of healthy normal resident skin microflora, preferably for stimulating the growth of healthy normal resident skin microflora belonging to the *Staphylococcus* genus, more preferably for stimulating the growth of *S. epidermidis*, and even more preferably for stimulating the growth of *S. epidermidis* without stimulating the growth of pathogenic microorganisms, in particular of *S. aureus*, said method comprising administering an effective dose of the peptide of the invention to the subject.

Additionally, the present invention further preferably relates to the use of the inventive peptide or compositions for inhibiting the growth of transient pathogenic skin microflora, preferably for inhibiting the growth of transient pathogenic skin microflora belonging to the *Staphylococcus* genus. In addition to this the present invention equally relates to a method of using the inventive peptide or compositions for inhibiting the growth of transient pathogenic skin microflora, preferably for inhibiting the growth of transient pathogenic skin microflora belonging to the *Staphylococcus* genus, more preferably for inhibiting the growth of *S. aureus*, and even more preferably for inhibiting the growth of *S. aureus* without inhibiting the growth of beneficial microorganisms, in particular of *S. epidermidis*, said method comprising administering an effective dose of the peptide of the invention to the subject, wherein said effective dose may be any one of a cosmetically effective dose, a prophylactically effective dose, or a therapeutically effective dose.

Also, the present invention concerns the use of a microorganism for the production of a peptide of the present invention, wherein the microorganism is preferably a prokaryote microorganism, more preferably one or more strains of bacteria, more preferably one or more lactic acid bacteria, and more preferably one or more bacteria of the genus *Lactobacillus*. In addition to this the present invention equally relates to a method of using a microorganism for the production of a peptide of the present invention, in particular by isolating the peptide of the invention or a precursor thereof from the microorganism, wherein the microorganism is preferably a prokaryote microorganism, more preferably one or more strains of bacteria, more preferably one or more lactic acid bacteria, more preferably one or more bacteria of the genus *Lactobacillus*, wherein more preferably the bacteria is selected from the group consisting of the *Lactobacillus* species *L. acidophilus*, *L. plantarum*, *L. reuteri*, *L. casei*, *L. paracasei*, *L. brevis*, *L. fermentum*, *L. buchneri*, *L. delbrückii*, preferably *L. delbrückii* ssp. *delbrückii*, and combinations of two or more thereof, wherein more preferably the *Lactobacillus* species is selected from the group consisting of *L. brevis*, preferably *L. brevis* having DSMZ accession number DSM 17247, DSM 17250, and mutants or derivatives thereof, *L. paracasei*, preferably *L. paracasei* having DSMZ accession number DSM 17248 and mutants or derivatives thereof, *L. fermentum*, preferably *L. fermentum* having DSMZ accession number DSM 17249 and mutants or derivatives thereof, *L. delbrückii* ssp. *delbrückii*, preferably *L. delbrückii* ssp. *delbrückii* having DSMZ accession number DSM 18006 and mutants or derivatives thereof, *L. buchneri*, preferably *L. buchneri* having DSMZ accession number DSM 18007 and mutants or derivatives thereof, and combinations of two or more thereof, wherein more preferably the *Lactobacillus* species is *L. brevis*, more preferably selected from the group consisting of *L. brevis* having DSMZ accession number DSM 17247, DSM 17250, and mutants or derivatives thereof, and wherein even more preferably the *Lactobacillus* species is *L. brevis* having DSMZ accession number DSM 17250 and/or mutants or derivatives thereof.

DETAILED DESCRIPTION

Thus, it has been surprisingly been found that a simple compound which is easily accessible may be provided for use in both cosmetic and pharmaceutical applications, in particular with respect to cosmetic skin care as well a with regard to the treatment and/or prophylaxis of both non-pathological and pathological skin conditions. Furthermore, it has quite unexpectedly been found that a simple compound may be provided for use as a medicament, in particular as an anti-inflammatory drug.

Therefore, in a first aspect, the present invention concerns a peptide of the following formula (I)

$$X_1(X_2)\text{-}X_3\text{-}X_4 \qquad (I)$$

or a salt or solvate thereof, wherein
$X_1$ is an amino acid residue comprising two or more NH-functionalities, and
$X_2$, $X_3$, and $X_4$ are, independently from one another, an amino acid residue, and
wherein the salt or solvate is preferably a physiologically acceptable salt or solvate.

Throughout this specification and the claims which follow, unless the context requires otherwise, the word "comprise", and variations such as "comprises" and "comprising", will be understood to imply the inclusion of a stated integer or step or constituent, or group of integers or steps or constituents, but not the exclusion of any other integer or step or constituent, or group of integers or steps or constituents.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

According to the present invention, the peptide of formula (I) comprises a tripeptide sequence $X_1\text{-}X_3\text{-}X_4$, wherein $X_1$ constitutes the N-terminus, and $X_4$ constitutes the C-terminus. Furthermore, the peptide contains an amino acid residue $X_2$ which is covalently bound to the side-chain of the amino acid residue $X_1$. In principle, there is no restriction according to the present invention regarding the covalent bond formed between $X_1$ and $X_2$, provided that $X_2$ is not covalently bound to the N-terminus of $X_1$. Consequently, the peptide of formula I does not, for example, comprise tetrapeptides or a tetrapeptide motif of the sequence $X_2\text{-}X_1\text{-}X_3\text{-}X_4$, wherein $X_2$ would be covalently bound to the N-terminal group of the N-terminus.

Within the meaning of the present invention, the terms "amino acid" and "amino acid residue" are not particularly restricted, and in general designate any conceivable compound containing one or more amino moieties and one or more carboxyl moieties, such as to be able to form peptidic bonds with one another. In particular, the terms "amino acid" and "amino acid residue" as employed herein includes and encompasses all of the naturally occurring amino acids, either in the D-, L-, allo-, or other stereoisomeric configurations if optically active, as well as any known or conceivable non-native, synthetic, and modified amino acids. According to preferred embodiments of the present invention, the optically active amino acids and amino acid residues are preferably in the D- and/or L-configuration, including racemic mixtures, wherein it is more preferred that the optically active amino acid and amino acid residues are in the L-configuration.

According to preferred embodiments of the present invention wherein the amino acid in $X_1$ is an alpha-amino acid, the N-terminus is accordingly constituted by the alpha-amino group thereof. According to alternatively preferred embodiments of the present invention wherein the amino acid in $X_1$ is not an alpha-amino acid, and wherein $X_1$ contains two or more amino groups, there is no general restriction as to which of the two or more amino groups constitutes the N-terminus, and is therefore not covalently bound to $X_2$. According to specific embodiments of said alternatively preferred embodiments, wherein $X_1$ further contains one or more side-chains, and the second and/or further amino group(s) is/are covalently bound to said one or more side-chains, it is preferred that the N-terminus is not an amino group which is present on a side-chain.

Thus, it has quite surprisingly been found that a peptide according to formula (I) containing a sequence of three amino acid residues, wherein a fourth amino acid is covalently bound to the amino acid of the N-terminus other than by the N-terminal group thereof, affords a peptide which may be advantageously employed in both cosmetic and pharmaceutical applications. In particular, as will be shown in the illustrative inventive examples below, it has quite unexpectedly been found that such a peptide may advantageously be used for both cosmetic and pharmaceutical treatment of the skin. Furthermore, the inventive peptide surprisingly shows an anti-inflammatory activity, such that it also proves to be advantageous for a variety of potential applications, in particular as a medicament in the prophylaxis and/or treatment of inflammatory conditions in addition to a variety of inflammation-related conditions and diseases. Thus, although a variety of smaller peptide sequences are known to be of a certain benefit in predominantly cosmetic applications such as e.g. disclosed in WO 2005/048968 A1, WO 00/43417 A1, U.S. Pat. No. 6,620,419 B1, and U.S. Pat. No. 6,492,326 B1, it has quite unexpectedly been found that the specific binding pattern in a peptide according to the present invention surprisingly leads to an unprecedented activity of a highly advantageous use and potential not only in non-therapeutic cosmetic applications but also as a medicament for the effective prophylaxis and/or treatment of numerous conditions and diseases.

According to preferred embodiments of the present invention, the term "amino acid" designates one or more amino acids selected from the group consisting of Arg, His, Lys, 3,6-Diaminohexanoic acid (Bly), N5-Aminocarbonylornithine (Cit), 2,4-Diaminobutanoic acid (Dab), 2,3-Diaminopropanoic acid (Dpr), 2,7-Diaminosuberic acid (Dsu), Homoarginine (Har), Homohistidine (Hhs), 5-Hydroxylysine (Hyl), Ornithine (Orn), Pyrrolysine (Pyl), Asn, Asp, Gln, Glu, 2-Aminoadipic acid (Aad), α-Asparagine (Aan), 2-Aminocapric acid (Aca), alpha-Glutamine (Agn), 2-Aminopimelic acid (Apm), gamma-Amino-beta-hydroxybenzenepentanoic acid (App), 2-Aminosuberic acid (Asu), beta-Aspartic acid (Bas), Diaminopimelic acid (Dpm), gamma-Glutamic acid (Ggu), gamma-Carboxyglutamic acid (Gla), Ala, Cys, Gly, Ile, Leu, Met, Phe, Pro, Ser, Thr, Trp, Tyr, Val, Scy, 2-Aminobutanoic acid (Abu), 2-Aminoheptanoic acid (Ahe), alpha-Aminoisobutyric acid (Aib), 2-Carboxyazetidine (Aze), beta-Alanine (Bal), 4-Amino-3-hydroxybutanoic acid (Bux), gamma-Amino-beta-hydroxycyclohexanepentanoic acid (Cap), 3-Cyclohexylalanine (Cha), 3-Sulfoalanine (Cya), S-Ethylthiocysteine (Edc), Pyroglutamic acid (Glp), Homocysteine (Hcy), Homophenylalanine (Hph), Homoserine (Hse), 4-Hydroxyproline (Hyp), 3-Hydroxyproline (3Hyp), alpha-Amino-2-indanacetic acid (Igl), Isovaline (Iva), 3-Hydroxy-4-methylproline (Mhp), 3-Naphthylalanine (Nal), Norleucine (Me), N-Benzylglycine (Nphe), Nortyrosine (Nty), Norvaline (Nva), 2-Carboxyoctahydroindole (Oic), Penicillamine (Pen), 2-Phenylglycine (Phg), 2-Carboxypiperidine (Pip), Phospho-L-serine (pSer), Phospho-L-threonine (pThr), Phospho-L-tyrosine (pTyr), Sarcosine (Sar), 1-Amino-1-carboxycyclopentane (Spg), Statine (4-amino-3-hydroxy-6-methylheptanoic acid) (Sta), 3-Thienylalanine (Thi), 3-Carboxylsoquinoline (Tic), 3-Methylvaline (Tle), epsilon-N-Trimethyllysine (Tml), 3-Thiazolylalanine (Tza), alpha-Amino-2,4-dioxopyrimidinepropanoic acid (Wil), and derivatives thereof.

Within the meaning of the present invention, a "derivative" of any amino acid or the "derivatization" thereof refers to any conceivable chemical modification thereof, provided that the derivative is capable of forming the same peptidic bonds as for the underivatized amino acid residue. According to preferred embodiments the term "derivative" refers to chemically modified amino acid residues having the same carbon chain(s) as the underivatized amino acid, and wherein and the amino and carbonyl functionalities present in the underivatized amino acid may be found at the same positions of the carbon chain(s) in the derivatized residues.

With respect to the types of chemical modifications which may be present in the amino acid derivatives, these preferably concern the replacement of hydrogen in C—H and/or N—H moieties and/or the replacement of terminal oxo, —OH, and/or —OR moieties, one or more of which are present in the underivatized amino acid residue. In particular, according to preferred derivatives of the amino acid residues wherein one or more hydrogen atoms in C—H moieties of the underivatized amino acid have been chemically modified, it is preferred that independently from one another the one or more hydrogen atoms are replaced with halogen, OH, alkyl, alkoxy, $NH_2$, alkylamino, dialkylamino, thiol, thioether, formyl, acyl, alkoxycarbonyl, or a derivative thereof, more preferably with F, Cl, Br, OH, $(C_1-C_3)$alkyl, $(C_1-C_3)$alkoxy, $NH_2$, $(C_1-C_3)$alkylamino, di$(C_1-C_3)$alkylamino, thiol, $(C_1-C_3)$thioether, formyl, $(C_1-C_3)$acyl, $(C_1-C_3)$alkoxycarbonyl, or a derivative thereof. Furthermore, according to preferred derivatives of the amino acid residues wherein one or more hydrogen atoms in N—H moieties of the underivatized amino acid have been chemically modified, it is preferred that independently from one another the one or more hydrogen atoms are replaced with halogen, alkyl, formyl, acyl, alkoxycarbonyl, or a derivative thereof, more preferably with F, $(C_1-C_3)$alkyl, formyl, $(C_1-C_3)$acyl, $(C_1-C_3)$alkoxycarbonyl, or a derivative thereof. Furthermore, according to preferred derivatives of the amino acid residues wherein one or more —OH, and/or —OR moieties of the underivatized amino acid have been chemically modified, it is preferred that independently from one another these have been modified to halogen, OH, alkyl, alkoxy, $NH_2$, alkylamino, dialkylamino, thiol, thioether, formyl, acyl, alkoxycarbonyl, or a derivative thereof, more preferably with F, Cl, Br, OH, $(C_1-C_3)$alkyl, $(C_1-C_3)$alkoxy, $NH_2$, $(C_1-C_3)$alkylamino, di$(C_1-C_3)$alkylamino, thiol, $(C_1-C_3)$thioether, formyl, $(C_1-C_3)$acyl, $(C_1-C_3)$alkoxycarbonyl, or a derivative thereof. Furthermore, according to preferred derivatives of the amino acid residues wherein one or more terminal oxo ligands of the underivatized amino acid have been chemically modified, it is preferred that terminal oxo is chemically modified to terminal thio, acetal, thioacetal, hemiacetal, or a derivative thereof.

According to the present invention, the peptide may be in any conceivable form, such as for example in the form of a neutral or zwitterionic compound, or in the form of a salt or solvate, wherein there is no particular restriction as to the type of salt or solvate which the peptide may be present. Within a preferred meaning of the present invention, the expression "salt" is understood as meaning both salts of carboxyl groups and also acid addition salts of amino groups of the peptide according to the invention. Salts of carboxyl groups preferably comprise inorganic salts, such as, for example, sodium, calcium, ammonium, iron and zinc salts, and/or salts with organic bases, such as, for example, amines such as triethanolamine, arginine, lysine, piperidine and the like. Furthermore, the salts of the present invention include acid addition salts, such as, for example, salts with mineral acids, such as hydrochloric acid or sulfuric acid and salts with organic acids, such as acetic acid and oxalic acid. The expression "solvate" on the other hand refers to any conceivable polar or non-polar solvent provided that it may form a solvate with the peptide of the present invention, including salts thereof. According to preferred embodiments, the solvate is selected from the group consisting of water, acetonitrile, dimethyl sulfoxide, methanol, propylene carbonate, ammonia, ethanol, and acetone, and mixtures of two or more thereof, more preferably from the group consisting of water, dimethyl sulfoxide, propylene carbonate, ethanol, and mixtures of two or more thereof.

It is, however, particularly preferred that in embodiments of the present invention in which the peptide is in the form of a salt or solvate, said salt or solvate is physiologically acceptable, in particular with respect to the systemic and/or topical application thereof, and even more preferably with respect to the topical application thereof.

According to a preferred embodiment of the present invention, $X_1$ is an amino acid residue selected from the group consisting of Arg, His, Lys, Bly, Cit, Dab, Dpr, Dsu, Har, Hhs, Hyl, Orn, Pyl, and derivatives thereof, more preferably from the group consisting of Dpr, Dab, Orn, Lys, Dsu, and derivatives thereof, more preferably from the group consisting of Dpr, Dab, Orn, Lys, and derivatives thereof, more preferably from the group consisting of Orn, Lys, and derivatives thereof, and wherein even more preferably $X_1$ is Lys or a derivative thereof.

Alternatively or in addition to the aforementioned preferred amino acid residues for $X_1$, and preferably in addition to the aforementioned preferred amino acid residues for $X_1$, it is further preferred according to the present invention that $X_2$ is an amino acid residue selected from the group consisting of Asn, Asp, Gln, Glu, Aad, Aan, Aca, Agn, Apm, App, Asu, Bas, Cit, Dpm, Dsu, Ggu, Gla, and derivatives thereof, more preferably from the group consisting of Asp, Glu, Aad, Apm, and derivatives thereof, more preferably from the group consisting of Asp, Glu, and derivatives thereof, and wherein even more preferably $X_2$ is Asp or a derivative thereof.

Thus, according to the present invention it is preferred that the fragment $X_1(X_2)$- of formula I is a combination of two amino acid residues selected from the group consisting of Arg(Asn)-, His(Asn)-, Lys(Asn)-, Bly(Asn)-, Cit(Asn)-, Dab (Asn)-, Dpr(Asn)-, Dsu(Asn)-, Har(Asn)-, Hhs(Asn)-, Hyl (Asn)-, Orn(Asn)-, Pyl(Asn)-, Arg(Asp)-, His(Asp)-, Lys (Asp)-, Bly(Asp)-, Cit(Asp)-, Dab(Asp)-, Dpr(Asp)-, Dsu (Asp)-, Har(Asp)-, Hhs(Asp)-, Hyl(Asp)-, Orn(Asp)-, Pyl (Asp)-, Arg(Gln)-, His(Gln)-, Lys(Gln)-, Bly(Gln)-, Cit (Gln)-, Dab(Gln)-, Dpr(Gln)-, Dsu(Gln)-, Har(Gln)-, Hhs (Gln)-, Hyl(Gln), Orn(Gln)-, Pyl(Gln)-, Arg(Glu)-, His (Glu)-, Lys(Glu)-, Bly(Glu)-, Cit(Glu)-, Dab(Glu)-, Dpr (Glu)-, Dsu(Glu)-, Har(Glu)-, Hhs(Glu)-, Hyl(Glu)-, Orn (Glu)-, Pyl(Glu)-, Arg(Aad)-, His(Aad)-, Lys(Aad)-, Bly (Aad)-, Cit(Aad)-, Dab(Aad)-, Dpr(Aad)-, Dsu(Aad)-, Har (Aad)-, Hhs(Aad)-, Hyl(Aad)-, Orn(Aad)-, Pyl(Aad)-, Arg (Aan)-, His(Aan)-, Lys(Aan)-, Bly(Aan)-, Cit(Aan)-, Dab (Aan)-, Dpr(Aan)-, Dsu(Aan)-, Har(Aan)-, Hhs(Aan)-, Hyl (Aan)-, Orn(Aan)-, Pyl(Aan)-, Arg(Aca)-, His(Aca)-, Lys (Aca)-, Bly(Aca)-, Cit(Aca)-, Dab(Aca)-, Dpr(Aca)-, Dsu (Aca)-, Har(Aca)-, Hhs(Aca)-, Hyl(Aca)-, Orn(Aca)-, Pyl (Aca)-, Arg(Agn)-, His(Agn)-, Lys(Agn)-, Bly(Agn)-, Cit (Agn)-, Dab(Agn)-, Dpr(Agn)-, Dsu(Agn)-, Har(Agn)-, Hhs (Agn)-, Hyl(Agn)-, Orn(Agn)-, Pyl(Agn)-, Arg(Apm)-, His (Apm)-, Lys(Apm)-, Bly(Apm)-, Cit(Apm)-, Dab(Apm)-, Dpr(Apm)-, Dsu(Apm)-, Har(Apm)-, Hhs(Apm)-, Hyl (Apm)-, Orn(Apm)-, Pyl(Apm)-, Arg(App)-, His(App)-, Lys (App)-, Bly(App)-, Cit(App)-, Dab(App)-, Dpr(App)-, Dsu (App)-, Har(App)-, Hhs(App)-, Hyl(App)-, Orn(App)-, Pyl (App)-, Arg(Asu)-, His(Asu)-, Lys(Asu)-, Bly(Asu)-, Cit (Asu)-, Dab(Asu)-, Dpr(Asu)-, Dsu(Asu)-, Har(Asu)-, Hhs (Asu)-, Hyl(Asu)-, Orn(Asu)-, Pyl(Asu)-, Arg(Bas)-, His (Bas)-, Lys(Bas)-, Bly(Bas)-, Cit(Bas)-, Dab(Bas)-, Dpr (Bas)-, Dsu(Bas)-, Har(Bas)-, Hhs(Bas)-, Hyl(Bas)-, Orn (Bas)-, Pyl(Bas)-, Arg(Cit)-, His(Cit)-, Lys(Cit)-, Bly(Cit)-, Cit(Cit)-, Dab(Cit)-, Dpr(Cit)-, Dsu(Cit)-, Har(Cit)-, Hhs (Cit)-, Hyl(Cit)-, Orn(Cit)-, Pyl(Cit)-, Arg(Dpm)-, His (Dpm)-, Lys(Dpm)-, Bly(Dpm)-, Cit(Dpm)-, Dab(Dpm)-, Dpr(Dpm)-, Dsu(Dpm)-, Har(Dpm)-, Hhs(Dpm)-, Hyl (Dpm)-, Orn(Dpm)-, Pyl(Dpm)-, Arg(Dsu)-, His(Dsu)-, Lys (Dsu)-, Bly(Dsu)-, Cit(Dsu)-, Dab(Dsu)-, Dpr(Dsu)-, Dsu (Dsu)-, Har(Dsu)-, Hhs(Dsu)-, Hyl(Dsu)-, Orn(Dsu)-, Pyl (Dsu)-, Arg(Ggu)-, His(Ggu)-, Lys(Ggu)-, Bly(Ggu)-, Cit (Ggu)-, Dab(Ggu)-, Dpr(Ggu)-, Dsu(Ggu)-, Har(Ggu)-, Hhs (Ggu)-, Hyl(Ggu)-, Orn(Ggu)-, Pyl(Ggu)-, Arg(Gla)-, His (Gla)-, Lys(Gla)-, Bly(Gla)-, Cit(Gla)-, Dab(Gla)-, Dpr (Gla)-, Dsu(Gla)-, Har(Gla)-, Hhs(Gla)-, Hyl(Gla)-, Orn (Gla)-, Pyl(Gla)-, and derivatives thereof.

More preferably, the fragment $X_1(X_2)$- of formula I is a combination of two amino acid residues selected from the group consisting of Lys(Asp)-, Dab(Asp)-, Dpr(Asp)-, Dsu (Asp)-, Orn(Asp)-, Lys(Glu)-, Dab(Glu)-, Dpr(Glu)-, Dsu (Glu)-, Orn(Glu)-, Lys(Aad)-, Dab(Aad)-, Dpr(Aad)-, Dsu (Aad)-, Orn(Aad)-, Lys(Apm)-, Dab(Apm)-, Dpr(Apm)-, Dsu(Apm)-, Orn(Apm)-, and derivatives thereof, more preferably from the group consisting of Lys(Asp)-, Dab(Asp)-, Dpr(Asp)-, Orn(Asp)-, Lys(Glu)-, Dab(Glu)-, Dpr(Glu)-, Orn(Glu)-, Lys(Aad)-, Dab(Aad)-, Dpr(Aad)-, Orn(Aad)-, Lys(Apm)-, Dab(Apm)-, Dpr(Apm)-, Orn(Apm)-, and derivatives thereof, more preferably from the group consisting of Lys(Asp)-, Orn(Asp)-, Lys(Glu)-, Orn(Glu)-, Lys (Aad)-, Orn(Aad)-, Lys(Apm)-, Orn(Apm)-, and derivatives thereof, and even more preferably from the group consisting of Lys(Asp)-, Orn(Asp)-, Lys(Glu)-, Orn(Glu)-, and derivatives thereof.

Alternatively or in addition to the aforementioned preferred amino acid residues for $X_1$ and/or $X_2$, and preferably in addition to the aforementioned preferred amino acid residues for $X_1$ and/or $X_2$, it is further preferred according to the present invention that $X_3$ is an amino acid residue selected from the group consisting of Ala, Cys, Gly, Ile, Leu, Met, Phe, Pro, Ser, Thr, Trp, Tyr, Val, Scy, Abu, Ahe, Aib, Aze, Bal, Bux, Cap, Cha, Cya, Edc, Glp, Hcy, Hph, Hse, Hyp, 3Hyp, Igl, Iva, Mhp, Nal, Nle, Nphe, Nty, Nva, Oic, Pen, Phg, Pip, pSer, pThr, pTyr, Sar, Spg, Sta, Thi, Tic, Tie, Tml, Tza, Wil, and derivatives thereof, more preferably from the group consisting of Ala, Aib, Abu, Nva, Nle, Ahe, and derivatives thereof, more preferably from the group consisting of Ala, Aib, Abu, Nva, and derivatives thereof, and wherein even more preferably $X_3$ is Ala or a derivative thereof.

Alternatively or in addition to the aforementioned preferred amino acid residues for $X_1$ and/or $X_2$, and preferably in addition to the aforementioned preferred amino acid residues for $X_1$ and/or $X_2$, it is further preferred according to the present invention that $X_4$ is an amino acid residue selected from the group consisting of Asn, Asp, Gln, Glu, Aad, Aan, Aca, Agn, Apm, App, Asu, Bas, Cit, Dpm, Dsu, Ggu, Gla, and derivatives thereof, more preferably from the group consisting of Asp, Glu, Aad, Apm, and derivatives thereof, more preferably from the group consisting of Asp, Glu, Aad, and derivatives thereof, and wherein even more preferably $X_4$ is Glu or a derivative thereof.

Therefore, according to preferred embodiments of the inventive peptide, $X_1$ is an amino acid residue selected from the group consisting of Arg, His, Lys, Bly, Cit, Dab, Dpr, Dsu, Har, Hhs, Hyl, Orn, Pyl, and derivatives thereof,
and/or, preferably and
wherein $X_2$ and $X_4$ are, independently from one another, an amino acid residue selected from the group consisting of Asn, Asp, Gln, Glu, Aad, Aan, Aca, Agn, Apm, App, Asu, Bas, Cit, Dpm, Dsu, Ggu, Gla, and derivatives thereof,
and/or, preferably and
wherein $X_3$ is an amino acid residue selected from the group consisting of Ala, Cys, Gly, Ile, Leu, Met, Phe, Pro, Ser, Thr, Trp, Tyr, Val, Scy, Abu, Ahe, Aib, Aze, Bal, Bux, Cap, Cha, Cya, Edc, Glp, Hcy, Hph, Hse, Hyp, 3Hyp, Igl, Iva, Mhp, NaI, Nle, Nphe, Nty, Nva, Oic, Pen, Phg, Pip, pSer, pThr, pTyr, Sar, Spg, Sta, Thi, Tic, Tle, Tml, Tza, Wil, and derivatives thereof.

As mentioned in the foregoing, there is no particular restriction regarding the covalent bond formed between $X_1$ and $X_2$, provided that the N-terminal group of the N-terminus present in $X_1$ does not engage in a covalent bond with $X_2$. Thus, apart from said restriction, $X_1$ and $X_2$ may be bound to one another via one or more covalent bonds, wherein the term "covalent bond" includes single, double, and triple bonds, wherein according to the present invention it is preferred that the term "covalent bond" designates a single or double bond, and even more preferably designates a single covalent bond. Furthermore, with respect to the one or more covalent bonds formed between $X_1$ and $X_2$ there is no particular restriction as to the types of atoms contained in $X_1$ and $X_2$ which engage in said one or more covalent bonds, provided that this does not include the specific nitrogen atom contained in the N-terminal group of the N-terminus of $X_1$. Thus, by way of example, the one or more covalent bonds include C—C, C—N, C—O, and C—S bonds, wherein the one or more covalent bonds formed between $X_1$ and $X_2$ is preferably one or more of a C—C, C—N, or C—O bond, more preferably of a C—C or C—N bond, and wherein the one or more covalent bonds preferably include one or more C—N bonds.

According to further preferred embodiments of the present invention, $X_1$ and $X_2$ are covalently bound by one or more C—N bonds, more preferably by one C—N bond, wherein even more preferably the C-atom of the C—N bond is a C-atom belonging to the $X_2$ amino acid residue, and the N-atom belongs to the one or more NH-functionalities of $X_1$ which is not the N-atom of the N-terminal group of the N-terminus of $X_1$. According to particularly preferred embodiments of the present invention, $X_1$ and $X_2$ are covalently bound by one or more amide bonds, preferably by one amide bond, wherein even more preferably the C-atom of the C(O)—N bond is a C-atom belonging to a carbonyl group of the $X_2$ amino acid residue, and the N-atom belongs to the one or more NH-functionalities of $X_1$ which is not the N-atom of the N-terminal group of the N-terminus of $X_1$.

Therefore, according to preferred embodiments of the present invention, $X_1$ and $X_2$ of the inventive peptide are bound to one another via an amide bond, wherein the amide bond is preferably formed by an N-moiety of the $X_1$ amino acid residue and a carbonyl-moiety of the $X_2$ amino acid residue.

According to embodiments of the present invention which are further preferred, $X_2$ is covalently bound to $X_1$ neither by the N-terminal amino group, nor by the C-terminal carboxyl or carbonyl group thereof, i.e. of the amino acid residue $X_1$, respectively. Thus, according to preferred embodiments wherein $X_1$ and $X_2$ are bound by an amide bond formed by an N-moiety of the $X_1$ amino acid residue and a carbonyl-moiety of the $X_2$ amino acid residue, it is further preferred that the carbonyl moiety of the $X_2$ amino acid moiety is not a carbonyl moiety of the C-terminal group thereof. Furthermore, according to preferred embodiments thereof, wherein the amino acid in $X_2$ is an α-amino acid, the C-terminus is accordingly constituted by the α-carboxyl or -carbonyl group thereof. According to alternatively preferred embodiments of the present invention wherein the amino acid in $X_2$ is not an α-amino acid, and wherein $X_2$ contains two or more carboxyl and/or carbonyl groups, there is no general restriction as to which of the two or more carboxyl and/or carbonyl groups constitutes the C-terminus, and is therefore not covalently bound to $X_1$ in accordance with the preferred embodiments of the present invention. According to specific embodiments of said alternatively preferred embodiments, wherein $X_2$ further contains one or more side-chains, and the second and/or further carboxyl and/or carbonyl group(s) is/are covalently bound to said one or more side-chains, it is preferred that the C-terminus is not a carboxyl or carbonyl group which is present on a side-chain.

Thus, according to further preferred embodiments, the invention relates to a peptide having the formula (II):

$$X_1(R^1\text{-}X_2\text{-}R^2)\text{-}X_3\text{-}X_4 \qquad (II)$$

wherein $X_2$ is covalently bound to $X_1$ neither by the N-terminal amino group, nor by the C-terminal carboxyl or carbonyl group thereof, i.e. of the amino acid residue $X_1$, respectively, and wherein $R^1$ and $R^2$ represent the optional derivatization of the N- and C-terminal groups, respectively.

In principle, $R^1$ and $R^2$ represent any suitable group which may be present at the N- and C-terminus of the amino acid residue $X_2$, wherein it is preferred that $R^1$ is H or a physiologically acceptable N-terminal blocking group, and $R^2$ is OH or a physiologically acceptable C-terminal blocking group. In particular, according to further preferred embodiments, $R^1$ is selected from the group consisting of H, alkyl, formyl, acyl, alkoxycarbonyl, and derivatives thereof, wherein more preferably $R^1$ is H, $(C_1\text{-}C_3)$alkyl, formyl, $(C_1\text{-}C_3)$acyl, $(C_1\text{-}C_3)$alkoxycarbonyl or a derivative thereof, more preferably H, $(C_1\text{-}C_3)$alkyl, or a derivative thereof, and wherein even more preferably $R^1$ is H.

Furthermore, according to preferred embodiments of the present invention wherein the inventive peptide has the formula II, it is further preferred that $R^2$ is selected from the group consisting of OH, alkyl, alkoxy, $NH_2$, alkylamino, dialkylamino, thiol, thioether, and derivatives thereof, wherein more preferably $R^2$ is OH, $(C_1\text{-}C_3)$alkoxy, $NH_2$, $(C_1\text{-}C_3)$alkylamino, di$(C_1\text{-}C_3)$alkylamino, thiol, $(C_1\text{-}C_3)$thioether, or a derivative thereof, more preferably OH, $(C_1\text{-}C_3)$alkoxy, $NH_2$, $(C_1\text{-}C_3)$alkylamino, di$(C_1\text{-}C_3)$alkylamino, or a derivative thereof, more preferably OH, $NH_2$, or a derivative thereof, more preferably OH or $NH_2$, and wherein even more preferably $R^2$ is $NH_2$.

Alternatively to or in addition to and preferably in addition to the aforementioned optional derivatization of the N-terminus and the preferred substitution of the C-terminus in $X_2$, respectively, the N-terminal group of the N-terminus in $X_1$ may also be derivatized. In principle, the N-terminal group in $X_1$ may optionally be derivatized in any conceivable fashion, wherein it is preferred that the optionally derivatized N-terminal group contains a physiologically acceptable N-terminal blocking group. In particular, according to further preferred embodiments, the N-terminal amino group is underivatized, i.e. is $NH_2$, or one or—independently from one another—both of the hydrogen of the N-terminal amino group are substituted by alkyl, formyl, acyl, alkoxycarbonyl, or a derivative thereof, more preferably by $(C_1-C_3)$alkyl, formyl, $(C_1-C_3)$acyl, $(C_1-C_3)$alkoxycarbonyl or a derivative thereof, and even more preferably by $(C_1-C_3)$alkyl or a derivative thereof. According to particularly preferred embodiments of the present invention, however, the N-terminus in $X_1$ is underivatized, i.e. is $NH_2$.

Furthermore, alternatively to or in addition to and preferably in addition to the aforementioned optional derivatization of the N-terminus and the preferred substitution of the C-terminus in $X_2$, respectively, the C-terminal group of the C-terminus in $X_4$ may also be derivatized. In principle, the C-terminal group in $X_4$ may optionally be derivatized in any conceivable fashion, wherein it is preferred that the optionally derivatized C-terminal group contains a physiologically acceptable C-terminal blocking group. In particular, according to further preferred embodiments, the C-terminal carboxyl group is underivatized, i.e. is C(O)—OH, or the hydroxyl moiety of the C-terminal carboxyl group is substituted by alkyl, alkoxy, $NH_2$, alkylamino, dialkylamino, thiol, thioether, or a derivative thereof, more preferably by $(C_1-C_3)$alkoxy, $NH_2$, $(C_1-C_3)$alkylamino, di$(C_1-C_3)$alkylamino, thiol, $(C_1-C_3)$thioether, or a derivative thereof, more preferably by $(C_1-C_3)$alkoxy, $NH_2$, $(C_1-C_3)$alkylamino, di$(C_1-C_3)$alkylamino, or a derivative thereof, wherein even more preferably the hydroxyl moiety of the C-terminal carboxyl group of $X_4$ is substituted by $NH_2$ or a derivative thereof, more preferably by $NH_2$.

Therefore, according to embodiments of the present invention which are further preferred, the peptide has the formula (II):

$$X_1(R^1-X_2-R^2)-X_3-X_4 \quad (II)$$

wherein $R^1$ is H or a physiologically acceptable N-terminal blocking group, and wherein $R^1$ is preferably H, alkyl, formyl, acyl, alkoxycarbonyl, or a derivative thereof, more preferably H, $(C_1-C_3)$alkyl, formyl, $(C_1-C_3)$acyl, $(C_1-C_3)$alkoxycarbonyl or a derivative thereof, more preferably H, $(C_1-C_3)$alkyl, or a derivative thereof, and wherein even more preferably $R^1$ is H, and/or, preferably and wherein $R^2$ is OH or a physiologically acceptable C-terminal blocking group, wherein preferably $R^2$ is OH, alkyl, alkoxy, $NH_2$, alkylamino, dialkylamino, thiol, thioether, or a derivative thereof, more preferably OH, $(C_1-C_3)$alkoxy, $NH_2$, $(C_1-C_3)$alkylamino, di$(C_1-C_3)$alkylamino, thiol, $(C_1-C_3)$thioether, or a derivative thereof, more preferably OH, $(C_1-C_3)$alkoxy, $NH_2$, $(C_1-C_3)$alkylamino, di$(C_1-C_3)$alkylamino, or a derivative thereof, more preferably OH, $NH_2$, or a derivative thereof, more preferably OH or $NH_2$, and wherein even more preferably $R^2$ is $NH_2$,
and/or, preferably and
wherein the C-terminal carboxyl group of the peptide in $X_4$ is functionalized to an amide, preferably to $X_4$—$NH_2$.

According to the present invention it is further preferred that the amino acid residues $X_1$, $X_2$, $X_3$, and $X_4$ of the inventive peptide are selected among the group consisting of amino acids naturally occurring in proteins and derivatives thereof, and in particular among the proteinogenic amino acids coded for in the genetic code. In particular, it is preferred that the amino acid residues $X_1$, $X_2$, $X_3$, and $X_4$ of the inventive peptide are selected from the group consisting of Arg, Asn, Ala, His, Asp, Cys, Lys, Gln, Gly, Glu, Ile, Leu, Met, Phe, Pro, Ser, Thr, Trp, Tyr, Val, Scy, and derivatives thereof.

According to a preferred embodiment of the present invention wherein the amino acid residues are selected from the group consisting of proteinogenic amino acids and derivatives thereof, $X_1$ is an amino acid residue selected from the group consisting of Arg, His, Lys, and derivatives thereof, wherein even more preferably $X_1$ is Lys or a derivative thereof. Alternatively or in addition to the aforementioned preferred amino acid residues for $X_1$, and preferably in addition to the aforementioned preferred amino acid residues for $X_1$, it is further preferred according to the present invention that $X_2$ is an amino acid residue selected from the group consisting of Asn, Asp, Gln, Glu, and derivatives thereof, wherein even more preferably $X_2$ is Asp or a derivative thereof.

Alternatively or in addition to the aforementioned preferred amino acid residues for $X_1$ and/or $X_2$, and preferably in addition to the aforementioned preferred amino acid residues for $X_1$ and/or $X_2$, it is further preferred according to the present invention that $X_3$ is an amino acid residue selected from the group consisting of Ala, Cys, Gly, Ile, Leu, Met, Phe, Pro, Ser, Thr, Trp, Tyr, Val, Scy, and derivatives thereof, more preferably from the group consisting of Gly, Ala, Val, Leu, Ile, Met, Pro, Phe, Trp, and derivatives thereof, more preferably from the group consisting of Gly, Ala, Val, Leu, Ile, and derivatives thereof, more preferably from the group consisting of Gly, Ala, Val, and derivatives thereof, and derivatives thereof, and wherein even more preferably $X_3$ is Ala or a derivative thereof.

Alternatively or in addition to the aforementioned preferred amino acid residues for $X_1$ and/or $X_2$, and preferably in addition to the aforementioned preferred amino acid residues for $X_1$ and/or $X_2$, it is further preferred according to the present invention that $X_4$ is an amino acid residue selected from the group consisting of Ala, Cys, Gly, Ile, Leu, Met, Phe, Pro, Ser, Thr, Trp, Tyr, Val, Scy, and derivatives thereof, more preferably from the group consisting of Asp, Asn, Glu, Gln, and derivatives thereof, more preferably from the group consisting of Asp, Glu, Gln, and derivatives thereof, more preferably from the group consisting of Glu, Gln, and derivatives thereof, and wherein even more preferably $X_4$ is Glu or a derivative thereof.

Therefore, according to preferred embodiments of the inventive peptide, $X_1$ is an amino acid residue selected from the group consisting of Arg, His, Lys, and derivatives thereof, $X_1$ preferably being Lys or a derivative thereof,
and/or, preferably and
$X_2$ is an amino acid residue selected from the group consisting of Asn, Asp, Gln, Glu, and derivatives thereof, $X_2$ preferably being Asp or a derivative thereof
and/or, preferably and
$X_3$ is an amino acid residue selected from the group consisting of Ala, Cys, Gly, Ile, Leu, Met, Phe, Pro, Ser, Thr, Trp, Tyr, Val, Scy, and derivatives thereof, preferably from the group consisting of Gly, Ala, Val, Leu, Ile, Met, Pro, Phe, Trp, and derivatives thereof, more preferably from the group consisting of Gly, Ala, Val, Leu, Ile, and derivatives thereof, more preferably from the group consisting of Gly, Ala, Val, and derivatives thereof, and wherein $X_3$ is even more preferably Ala or a derivative thereof, and/or, preferably and $X_4$ is an amino acid residue selected from the group consisting of Ala, Cys, Gly, Ile, Leu, Met, Phe, Pro, Ser, Thr, Trp, Tyr, Val, Scy, and derivatives thereof, preferably from the group consisting of Asp, Asn, Glu, Gln, and derivatives thereof, more preferably from the group consisting of Asp, Glu, Gln, and derivatives thereof, more preferably from the group consisting of Glu, Gln, and derivatives thereof, and wherein $X_4$ is even more preferably Glu or a derivative thereof.

With respect to the preferred embodiments of the present invention wherein the amino acid residues $X_1$, $X_2$, $X_3$, and $X_4$ of the inventive peptide are selected from the group consisting of amino acids naturally occurring in proteins and derivatives thereof, and in particular among the proteinogenic amino acids and derivatives thereof, said proteins also comprise embodiments wherein the protein is contained as a sequence motif in a larger protein or protein fragment or derivative thereof. Thus, according to said preferred embodiments, the inventive peptide may be linked via the N-terminus of $X_1$ and/or via the C-terminus of $X_4$ to one or more further proteinogenic amino acids and/or to one or more peptide or peptide moieties. In general, according to said preferred embodiments of the present invention, there is no particular restriction as to the number of further proteinogenic amino acids to which the inventive peptide may be linked or to the type and size of the peptide or peptide moieties to which it may be further bound via C- and/or N-terminal peptide bonds. Thus, by way of example, the inventive peptide may be linked to or comprised in a larger polypeptide or protein, such that the resulting polypeptide or protein may contain anywhere from 5 to 200 amino acid residues, wherein it is preferred according to said embodiments that the larger polypeptide or protein in which the inventive peptide is bound contains from 5 to 100 amino acid residues, more preferably from 5 to 50 amino acid residues, more preferably from 5 to 20 amino acid residues, more preferably from 5 to 10 amino acid residues, and even more preferably from 5 to 7 amino acid residues.

Alternatively, according to preferred embodiments of the present invention wherein the amino acid residues $X_1$, $X_2$, $X_3$, and $X_4$ of the inventive peptide are selected from the group consisting of amino acids naturally occurring in proteins and derivatives thereof, and in particular among the proteinogenic amino acids and derivatives thereof, the inventive peptide is a tetrapeptide which is not further contained as a sequence motif in a larger polypeptide or protein, wherein the C- and N-terminal groups of the tetrapeptide in $X_1$ and $X_2$ may be underivatized or derivatized according to any of the aforementioned embodiments and preferred embodiments relating to the derivatization of the C- and N-termini.

According to a particularly preferred embodiment of the present invention, $X_1$ is Lys or a derivative thereof, $X_2$ is Asp or a derivative thereof, $X_3$ is Ala or a derivative thereof, and $X_4$ is Glu or a derivative thereof, wherein more preferably $X_1$ is Lys, $X_2$ is Asp, $X_3$ is Ala, and $X_4$ is Glu. According to said embodiments it is further preferred that Asp and Lys are bound via their respective side chains in the form of an isopeptide bond, wherein the beta-carboxyl moiety of Asp forms a peptidic bond with the ε-amino moiety of Lys via condensation thereof. Furthermore, according to said preferred embodiment it is yet further preferred that the C-terminal carboxyl group of Asp is underivatized or amidated, wherein the C-terminus is preferably amidated, wherein even more preferably the —OH moiety of the C-terminal carboxyl group is substituted by $NH_2$.

Therefore, according to a particularly preferred embodiment of the present invention, the peptide has the following formula (III):

wherein $R^2$ is OH or $NH_2$, and preferably $NH_2$.

As mentioned in the foregoing with respect to preferred embodiments of the present invention, wherein the amino acid residues are selected from the group consisting of amino acids naturally occurring in proteins and derivatives thereof, the particularly preferred amino acid sequence motif according to formula III may also be linked via the N-terminus of Lys and/or via the C-terminus of Glu to one or more further proteinogenic amino acids and/or to one or more peptide or peptide moieties as described with respect to the embodiments and preferred embodiments in the foregoing.

According to the present invention it is however preferred that the peptide according to formula III is a tetrapeptide which is not further contained as a sequence motif in a larger polypeptide or protein, wherein furthermore the C- and N-terminal groups of the tetrapeptide in Glu and Lys may be underivatized or derivatized according to any of the aforementioned embodiments and preferred embodiments relating to the derivatization of the C- and N-termini. In particular, the N-terminal amino group in Lys may optionally be derivatized to contain a physiologically acceptable N-terminal blocking group, wherein preferably or one or—independently from one another—both of the hydrogen of the N-terminal $NH_2$ group are substituted by alkyl, formyl, acyl, alkoxycarbonyl, or a derivative thereof, more preferably by $(C_1-C_3)$alkyl, formyl, $(C_1-C_3)$acyl, $(C_1-C_3)$alkoxycarbonyl or a derivative thereof, and even more preferably by $(C_1-C_3)$alkyl or a derivative thereof. More specifically, the N-terminal amino group of the peptide in Lys is preferably $NR^5R^6$, wherein $R^5$ and $R^6$ are independently from one another H or alkyl, preferably H or $(C_1-C_3)$alkyl. According to particularly preferred embodiments of the present invention, however, the N-terminus in Lys is underivatized. Furthermore, the C-terminal carboxyl group in Glu may also be optionally derivatized to contain a physiologically acceptable C-terminal blocking group, wherein preferably the hydroxyl moiety of the C-terminal carboxyl group is substituted by alkyl, alkoxy, $NH_2$, alkylamino, dialkylamino, thiol, thioether, or a derivative thereof, more preferably by $(C_1-C_3)$alkoxy, $NH_2$, $(C_1-C_3)$alkylamino, di$(C_1-C_3)$alkylamino, thiol, $(C_1-C_3)$thioether, or a derivative thereof, more preferably by $(C_1-C_3)$alkoxy, $NH_2$, $(C_1-C_3)$alkylamino, di$(C_1-C_3)$alkylamino, or a derivative thereof, and wherein even more preferably the hydroxyl moiety of the C-terminal carboxyl group of $X_4$ is substituted by $NH_2$ or a derivative thereof. More specifically, Glu is preferably functionalized to an amide Glu-$NR^3R^4$, wherein $R^3$ and $R^4$ are independently from one another H or alkyl, preferably H or $(C_1-C_3)$alkyl, wherein even more preferably $R^3$ and $R^4$ are H.

Therefore, according to further preferred embodiments of the present invention, the inventive peptide has the formula (III):

wherein $R^2$ is OH or $NH_2$, and preferably $NH_2$, and
wherein the C-terminal carboxyl group of the peptide in Glu is preferably functionalized to an amide Glu-$NR^3R^4$,
wherein $R^3$ and $R^4$ are independently from one another H or alkyl, preferably H or $(C_1-C_3)$alkyl, wherein even more preferably $R^3$ and $R^4$ are H, and/or, preferably and
wherein the N-terminal amino group of the peptide in Lys is preferably $NR^5R^6$,
wherein $R^5$ and $R^6$ are independently from one another H or alkyl, preferably H or $(C_1-C_3)$alkyl, wherein even more preferably $R^5$ and $R^6$ are H.

In particular, according to a particularly preferred embodiment thereof, the peptide has the formula IV:

 (IV)

Accordingly, a tetrapeptide having the following chemical structure (V) is particularly preferred according to the present invention:

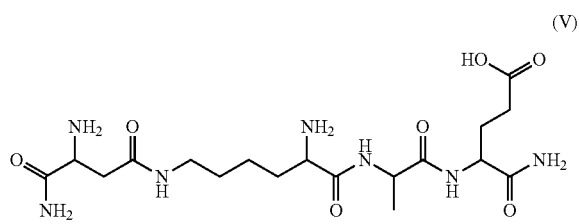 [SMILES: CC(NC(=O)C(N)CCCCNC(=O)CC(N)C(N)=O)C(=O)NC(CCC(=O)O)C(N)=O] (V)

In general, the peptide of the present invention may be obtained by any conceivable means using any of the methods well known in the art such as by chemical synthesis, wherein said synthesis may in part or entirely rely on biotechnological methods using recombinant strains or cultures. In particular, the small size of the inventive peptides is particularly advantageous since it allows for the use of cost-effective industrial synthetic methodologies. Their demonstrated high activity permits the commercial use in a large number of cosmetic or (dermo)pharmaceutical products in a cost-efficient manner. The peptide can however also be obtained by fermentation of one or more strains of bacteria, modified or not by genetic engineering, to produce the sought sequences or at least fragments thereof.

In addition to these production methods, the peptide can also be obtained by extraction of proteins of animal or vegetable origin, preferably vegetable, adapted to contain these sequences in their structure, which may be followed by controlled hydrolysis, enzymatic or not, which frees the desired peptide fragment. To carry out the invention, it is possible but not necessary, either to extract the proteins in question first and then to hydrolyze them, or to carry out hydrolysis first on a raw extract and to purify the peptide fragments. There can also be used the hydrolysate without extracting from it the peptide fragments in question, by ensuring however the stopping of the enzynamic hydrolysis reaction timewise and determining the presence of the peptides in question by suitable analytic means such as radioactivity tracing, immunofluorescence or immunoprecipitation with specific antibodies, and the like.

According to a preferred embodiment of the present invention, the inventive peptide is obtained from a microorganism, preferably from a prokaryote, and in particular from one or more strains of bacteria. According to the present invention it is particularly preferred that the microorganism used for producing the inventive peptide is a microorganism belonging to the group of lactic acid bacteria. The term "microorganism belonging to the group of lactic acid bacteria" encompasses (a) microorganism(s) which belong(s) to bacteria, in particular belonging to gram-positive fermentative eubacteria, more particularly belonging to the family of lactobacteriaceae including lactic acid bacteria. Lactic acid bacteria are from a taxonomical point of view divided up into the subdivisions of *Streptococcus*, *Leuconostoc*, *Pediococcus*, *Lactococcus* and *Lactobacillus*. The microorganism of the present invention is preferably a *Lactobacillus* species. Members of the lactic acid bacteria group normally lack porphyrins and cytochromes, do not carry out electron-transport phosphorylation and hence obtain energy only by substrate-level phosphorylation. I.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the bacteria preferably used in the present invention are preferably aerotolerant anaerobic lactic acid bacteria, preferably belonging to the genus of *Lactobacillus*.

It is further preferred according to the present invention that the microorganism used is a probiotic *Lactobacillus* species. The term "probiotic" in the context of the present invention means that the microorganism has a beneficial effect on health if it is topically applied to the skin. Preferably, a "probiotic" microorganism is a live microorganism which, when topically applied to the skin, is beneficial for health of this tissue.

In a preferred embodiment the microorganism used in the production of the inventive protein belongs to the species of selected from the group consisting of the *Lactobacillus* species *L. acidophilus*, *L. plantarum*, *L. reuteri*, *L. casei*, *L. paracasei*, *L. brevis*, *L. fermentum*, *L. buchneri*, *L. delbrückii*. However, the *Lactobacillus* species are not limited thereto.

According to a particularly preferred embodiment of the present invention, the microorganism which is employed is selected from the group of *Lactobacillus* species consisting of *L. brevis*, *L. paracasei*, *L. fermentum*, *L. delbrückii* ssp. *delbrückii*, *L. buchneri*, and combinations of two or more thereof. In particular, the group of *Lactobacillus* species preferably consists of *L. brevis* having DSMZ accession number DSM 17247 and/or DSM 17250, *L. paracasei* having DSMZ accession number DSM 17248, *L. fermentum* having DSMZ accession number DSM 17249, *L. delbrückii* ssp. *delbrückii* having DSMZ accession number DSM 18006, *L. buchneri* having DSMZ accession number DSM 18007, including mutants or derivatives thereof. Even more preferably, the *Lactobacillus* species is *L. brevis*, more preferably selected from the group consisting of *L. brevis* having DSMZ accession number DSM 17247, DSM 17250, and mutants or derivatives thereof, wherein even more preferably the *Lactobacillus* species is *L. brevis* having DSMZ accession number DSM 17250 and/or mutants or derivatives thereof. The aforementioned deposits were performed at the Deutsche Sammlung für Mikroorganismen and Zellkulturen (DSMZ) pursuant to the terms of the Budapest treaty on the international recognition of the deposit of microorganisms for the purposes of patent procedures. Furthermore, within the meaning of the present invention, a mutant or derivative of the above-mentioned deposited *Lactobacillus* strains designates any conceivable mutants or derivatives having retained their capability to be used in the production of the inventive peptide.

Therefore, the present invention further relates to the use of a microorganism for the production of the inventive peptide according to embodiments and preferred embodiments described in the foregoing, wherein the microorganism is preferably a prokaryote microorganism, more preferably one or more strains of bacteria, more preferably one or more lactic acid bacteria, more preferably one or more bacteria of the genus *Lactobacillus*, wherein more preferably the bacteria is selected from the group consisting of the *Lactobacillus* species *L. acidophilus*, *L. plantarum*, *L. reuteri*, *L. casei*, *L.*

*paracasei, L. brevis, L. fermentum, L. buchneri, L. delbrückii*, preferably *L. delbrückii* ssp. *delbrückii*, and combinations of two or more thereof, wherein more preferably the *Lactobacillus* species is selected from the group consisting of *L. brevis*, preferably *L. brevis* having DSMZ accession number DSM 17247, DSM 17250, and mutants or derivatives thereof, *L. paracasei*, preferably *L. paracasei* having DSMZ accession number DSM 17248 and mutants or derivatives thereof, *L. fermentum*, preferably *L. fermentum* having DSMZ accession number DSM 17249 and mutants or derivatives thereof, *L. delbrückii* ssp. *delbrückii*, preferably *L. delbrückii* ssp. *delbrückii* having DSMZ accession number DSM 18006 and mutants or derivatives thereof, *L. buchneri*, preferably *L. buchneri* having DSMZ accession number DSM 18007 and mutants or derivatives thereof, and combinations of two or more thereof, wherein more preferably the *Lactobacillus* species is *L. brevis*, more preferably selected from the group consisting of *L. brevis* having DSMZ accession number DSM 17247, DSM 17250, and mutants or derivatives thereof, and wherein even more preferably the *Lactobacillus* species is *L. brevis* having DSMZ accession number DSM 17250 and/or mutants or derivatives thereof.

In general, regarding the inventive use of a microorganism for the production of the inventive peptide, there is no particular restriction as to the method of obtaining the inventive peptide from the microorganism, provided that the peptide or a precursor thereof is obtained in a form in a form in which the inventive peptide may be employed for achieving the effects described herein, in particular with respect to its use in cosmetic and pharmaceutical applications. In particular, the use of a microorganism for the production of the inventive peptide preferably involves its effective isolation from the microorganism by any suitable means known to the skilled person.

According to a preferred embodiment, a lysate of the microorganism is first obtained, after which the inventive peptide is won from the lysate in a subsequent step. Within the meaning of the present invention, the term "lysate" designates a solution or suspension in an aqueous medium of cells of the one or more microorganisms which may be used according to the present invention which have been suitably severed or an extract thereof. However, the term should not be construed in any limiting way. In particular, in addition to the inventive peptide or to one or more suitable precursors thereof, the cell lysate regularly further comprises, e.g., macromolecules, like DNA, RNA, other proteins and peptides, carbohydrates, lipids and the like and/or micromolecules such as amino acids, sugars, lipid acids and the like, or fractions thereof. Furthermore, said lysate regularly comprises cell debris which may be of smooth or granular structure.

Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not essential to the present invention and thus any method that can achieve lysis of the cells of the microorganisms which are preferably used in the present invention may be employed. Thus, by way of example, the opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized. For example, the cells of the microorganisms preferably used in the present invention are lysed by freezing and thawing, more preferably freezing at temperatures of at most −70° C. and thawing at temperatures of at least 30° C., particularly freezing is preferred at temperatures of at most −75° C. and thawing is preferred at temperatures of at least 35° C. and most preferred are temperatures for freezing of at most −80° C. and temperatures for thawing of at least 37° C. It is also preferred that said freezing/thawing is repeated one or more times, more preferably two or more times, and even more preferred three or more times, wherein particularly preferably the procedure is repeated 4 or more times and even more preferably 5 or more times.

Preferably, the aqueous medium used for the lysates as described is water, physiological saline, or a buffer solution. An advantage of a bacterial cell lysate is that it can be easily produced and stored cost efficiently since less technical facilities are needed.

According to the invention, lysates are also preparations of fractions of molecules from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates.

The proteins of the present invention may also suitably be produced from a filtrate of the microorganisms used in the present invention, preferably of the *Lactobacillus* species disclosed herein. Within the meaning of the present invention, the term "filtrate" means a cell-free solution or suspension of the microorganisms used in the present invention which has been obtained as supernatant of a centrifugation procedure of a culture of the microorganisms used in the present invention in any appropriate liquid, medium or buffer known to the person skilled in the art. However, the term should not be construed in any limiting way. In particular, a filtrate regularly further comprises, e.g., macromolecules, like DNA, RNA, proteins, peptides, carbohydrates, lipids and the like and/or micromolecules, like amino acids, sugars, lipid acids and the like, or fractions of it. Methods for preparing filtrates of microorganism are known in the art. In addition, "filtrate" relates to various methods known in the art. The exact method is not essential and any method that can achieve filtration of the cells of the microorganism used in the production of the inventive peptide may be employed.

Furthermore, according to the present invention also any part of the cells of the microorganisms used in the present invention may be used for producing the inventive peptide, wherein preferably a membrane fraction is employed as obtained by membrane-preparation. Membrane preparations of microorganisms, and in particular of microorganisms belonging to the genus of *Lactobacillus* can be obtained by methods known in the art, for example, by employing the method described by Rollan et al. in Int. J. Food Microbiol. 70 (2001), 303-307, by Matsuquchi et al. in Clin. Diagn. Lab. Immunol. 10 (2003), 259-266, by Stentz et al. in Appl. Environ. Microbiol. 66 (2000), 4272-4278, or by Varmanen et al. in J. Bacteriology 182 (2000), 146-154. Alternatively, also a whole cell preparation may be used.

The present invention also provides the peptide of the present invention for use as a medicament.

The term "medicament" as used herein refers to a formulation of the peptide of the invention or a composition comprising it wherein said peptide is the pharmaceutical active compound. The peptide may be formulated in liquid, dry, gaseous or gel form. If the peptide is formulated in dry form, a lyophilized form is preferably envisaged. If a liquid formulation is envisaged, the peptide is preferably a component of a pharmaceutical composition which in addition to the peptide comprises a suitable solvent as a liquid pharmaceutical acceptable carrier. In gaseous form, the peptide can be included into an aerosol.

The term "pharmaceutically acceptable carrier" refers to a diluent, adjuvant, excipient, or vehicle with which the peptide is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of, e.g., solutions, suspensions, emulsion, powders, sustained-release formulations and the like. Examples of suitable pharmaceutical carriers are described in "Remington's Pharmaceutical Sciences" by E. W. Martin. Some other examples of substances which can serve as pharmaceutical carriers are sugars, such as glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present. It is also advantageous to administer the active ingredients in encapsulated form, e.g. as cellulose encapsulation, in gelatine, with polyamides, niosomes, wax matrices, with cyclodextrins or liposomally encapsulated. Preferred pharmaceutical acceptable carriers are also lactose, terra alba, sucrose, talc, gelatin, agar, pectin, acacia, magnesium stearate, stearic acid and the like as solid carriers and phosphate buffered saline solution, syrup, oil, water, emulsions, various types of wetting agents, and the like as liquid carriers. The carriers shall be pharmaceutically acceptable in that they shall not affect the biological properties of other ingredients and, in particular, the peptide of the invention, and shall be biocompatible upon administration to a subject, in particular, non-toxic and/or non-immunogenic.

Moreover, the pharmaceutical composition could comprise further ingredients such as stabilizers, sustained release agents, further drugs, and the like. Preferred stabilizers are protein stabilizers (e.g., human serum albumin (HSA)) or non-protein stabilizers. Sustained release agents are well known to the art and, preferably, include glyceryl monostearate or glyceryl distearate alone or with a wax. Further ingredients also encompass preservatives, perfumes, antifoams, dyes, pigments, thickeners, surface-active substances, emulsifiers, emollients, finishing agents, fats, oils, waxes or other customary constituents of a dermatological formulation, such as alcohols, polyols, polymers, foam stabilizers, solubility promoters, electrolytes, organic acids, organic solvents, or silicone derivatives.

The medicament according to the invention may comprise emollients. Emollients may be used in amounts which are effective to prevent or relieve dryness. Useful emollients include, without limitation: hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; phospholipids; sterols; and amides. Thus, for example, typical emollients include mineral oil, especially mineral oils having a viscosity in the range of 50 to 500 SUS (Saybolt Universal second), lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purcellin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12-C15) alcohols, the octanoates and decanoates of alcohols and polyalcohols such as those of glycol and glycerol, and ricin-oleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

Moreover, the medicament according to the invention may also comprise emulsifiers. Emulsifiers (i.e., emulsifying agents) are preferably used in amounts effective to provide uniform blending of ingredients of the composition. Useful emulsifiers include (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl surfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate; and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol. The selection of emulsifiers is exemplarily described in Schrader, Grundlagen and Rezepturen der Kosmetika, Hüthig Buch Verlag, Heidelberg, $2^{nd}$ edition, 1989, $3^{rd}$ part.

The medicament according to the invention may also include a surfactant. Suitable surfactants may include, for example, those surfactants generally grouped as cleansing agents, emulsifying agents, foam boosters, hydrotropes, solubilizing agents, suspending agents and nonsurfactants (facilitates the dispersion of solids in liquids). The surfactants are usually classified as amphoteric, anionic, cationic and nonionic surfactants. Amphoteric surfactants include acylamino acids and derivatives and N-alkylamino acids. Anionic surfactants include: acylamino acids and salts, such as, acylglutamates, acylpeptides, acylsarcosinates, and acyltaurates; carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Cationic surfactants include: alkylamines, alkyl imidazolines, ethoxylated amines, and quaternaries (such as, alkylbenzyldimethylammonium salts, alkyl betaines, heterocyclic ammonium salts, and tetra alkylammonium salts). And nonionic surfactants include: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

Furthermore, the medicament according to the invention may also comprise a film former. Suitable film formers which are used in accord with the invention keep the composition smooth and even and include, without limitation: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like. Generally, film formers can be used in amounts of about 0.1% to about 10% by weight of the total composition with about 1% to about 8% being preferred and about 0.1% to about 5% being most preferred. Humectants can also be used in effective amounts, including: fructose; glucose; glulamic acid; glycerin; honey; maltitol; methyl gluceth-10; methyl gluceth-20; propylene glycol; sodium lactate; sucrose; and the like.

Of course, the medicament of the present invention can also comprise a preservative. Preservatives according to certain compositions of the invention include, without limitation: butylparaben; ethylparaben; imidazolidinyl urea; methylparaben; O-phenylphenol; propylparaben; quaternium-14; quaternium-15; sodium dehydroacetate; zinc pyrithione; and the like. The preservatives are used in amounts effective to prevent or retard microbial growth. Generally, the preservatives are used in amounts of about 0.1% to about 1% by weight of the total composition with about 0.1% to about 0.8% being preferred, and about 0.1% to about 0.5% being most preferred.

The medicament according to the invention may also comprise a perfume. Perfumes (fragrance components) and colorants (coloring agents) well known to those skilled in the art may be used in effective amounts to impart the desired fragrance and color to the compositions of the invention.

Furthermore, the medicament according to the present invention may also comprise a wax. Suitable waxes which are useful in accord with the invention include: animal waxes, such as beeswax, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Animal, plant, and some mineral waxes are primarily esters of a high molecular weight fatty alcohol with a high molecular weight fatty acid. For example, the hexadecanoic acid ester of tricontanol is commonly reported to be a major component of beeswax. Other suitable waxes according to the invention include the synthetic waxes including polyethylene polyoxyethylene and hydrocarbon waxes derived from carbon monoxide and hydrogen. Representative waxes also include: cerosin; cetyl esters; hydrogenated jojoba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sulfurized jojoba oil; synthetic beeswax; synthetic jojoba oils; trihydroxystearin; cetyl alcohol; stearyl alcohol; cocoa butter; fatty acids of lanolin; mono-, di- and 25 triglycerides which are solid at 25° C., e.g., glyceryl tribehenate (a triester of behenic acid and glycerine) and C19-C36 acid triglyceride (a mixture of triesters of C19-C36 carboxylic acids and glycerine) available from Croda, Inc., New York, N.Y. under the tradenames Syncrowax HRC and Syncrowax HGL-C, respectively; fatty esters which are solid at 25° C.; silicone waxes such as methyloctadecaneoxypolysiloxane and poly (dimethylsiloxy) stearoxysiloxane; stearyl mono- and diethanolamide; rosin and its derivatives such as the abietates of glycol and glycerol; hydrogenated oils solid at 25° C.; and sucroglycerides. Thickeners (viscosity control agents) which may be used in effective amounts in aqueous systems include: algin; carbomers such as carbomer 934, 934P, 940 and 941; cellulose gum; cetearyl alcohol, cocamide DEA, dextrin; gelatin; hydroxyethylcellulose; hydroxypropylcellulose; hydroxypropyl methylcellulose; magnesium aluminum silicate; myristyl alcohol; oat flour; oleamide DEA; oleyl alcohol; PEG-7M; PEG-14M; PEG-90M; stearamide DEA; stearamide MEA; stearyl alcohol; tragacanth gum; wheat starch; xanthan gum; and the like in the above list of thickeners, DEA is diethanolamine, and MEA is monoethanolamine. Thickeners (viscosity control agents) which may be used in effective amounts in nonaqueous systems include aluminum stearates; beeswax; candelilla wax; carnauba; ceresin; cetearyl alcohol; cetyl alcohol; cholesterol; hydrated silica; hydrogenated castor oil; hydrogenated cottonseed oil;

hydrogenated soybean oil; hydrogenated tallow glyceride; hydrogenated vegetable oil; hydroxypropyl cellulose; lanolin alcohol; myristyl alcohol; octytdodecyl stearoyl sulfate; oleyl alcohol; ozokerite; microcrystalline wax; paraffin, pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like. Customary native and synthetic thickeners or gel formers in formulations are crosslinked polyacrylic acids and derivatives thereof, polysaccharides, such as xanthane gum or alginates, carboxymethylcellulose or hydroxycarboxymethylcellulose, hydrocolloids such as gum Arabic or montmorillonite minerals, such as bentonites or fatty alcohols, polyvinyl alcohol and polyvinlypyrrolidone.

Other ingredients which can be added or used in medicament according to the invention in amounts effective for their intended use, include: biological additives to enhance performance or consumer appeal such as amino acids, proteins, vanilla, aloe extract, bioflavinoids, and the like; buffering agents, chelating agents such as EDTA; emulsion stabilizers; pH adjusters; opacifying agents; and propellants such as butane carbon dioxide, ethane, hydrochlorofluorocarbons 22 and 142b, hydrofluorocarbon 152a, isobutane, isopentane, nitrogen, nitrous oxide, pentane, propane, and the like.

Furthermore, the medicament according to the invention may also comprise compounds which have an antioxidative, free-radical scavenger, skin moisturizing or moisture-retaining, antierythematous, antiinflammatory or antiallergic action, in order to supplement or enhance their action. In particular, these compounds can be chosen from the group of vitamins, plant extracts, alpha- and beta-hydroxy acids, ceramides, antiinflammatory, antimicrobial or UV-filtering substances, and derivatives thereof and mixtures thereof. Advantageously, preparations according to the invention can also comprise substances which absorb UV radiation in the UV-B and/or UV-A region. The lipid phase is advantageously chosen from the group of substances of mineral oils, mineral waxes, branched and/or unbranched hydrocarbons and hydrocarbon waxes, triglycerides of saturated and/or unsaturated, branched and/or unbranched C8-C24-alkanecarboxylic acids; they can be chosen from synthetic, semisynthetic or natural oils, such as olive oil, palm oil, almond oil or mixtures; oils, fats or waxes, esters of saturated and/or unsaturated, branched and/or unbranched C3-C30-alkane carboxylic acids and saturated and/or unsaturated, branched and/or unbranched C3-C30-alcohols, from aromatic carboxylic acids and saturated and/or unsaturated, branched and/or unbranched C3-C30-alcohols, for example isopropyl myristate, isopropyl stearate, hexyldecyl stearate, oleyl oleate; and also synthetic, semisynthetic and natural mixtures of such esters, such as jojoba oil, alkyl benzoates or silicone oils, such as, for example, cyclomethicone, dimethylpolysiloxane, diethylpolysiloxane, octamethylcyclo-tetrasiloxane and mixtures thereof or dialkyl ethers.

The medicament may be formulated dependent on the desired mode of administration. These procedures may involve mixing, granulating, and compression, or dissolving the ingredients as appropriate to the desired preparation. It will be appreciated that the form and character of the pharmaceutical acceptable carrier is dictated by the amount of active ingredient with which it is to be combined, the route of administration, and other well-known variables. Details are well known in the art, see, e.g., Remington's Pharmaceutical Sciences, Mack Publishing Company, Easton, Pa.

The medicament according to the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Forms suitable for topical application include, e.g., a paste, an ointment, a lotion, a cream, a gel or a transdermal patch. A suitable paste comprises, e.g., petroleum, soft white paraffin, yellow petroleum jelly and glycerol. A suitable ointment comprises the peptide as active ingredient suspended or dissolved in a carrier such as, one or more of glycerol, mineral oil, liquid oil, liquid petroleum, white petroleum, yellow petroleum jelly, propylene glycol, alcohols, triglycerides, fatty acid esters such as cetyl ester, polyoxyethylene polyoxypropylene compound, waxes such as white wax and yellow beeswax, fatty acid alcohols such as cetyl alcohol, stearyl alcohol and cetylstearylalcohol, fatty acids such as stearic acid, cetyl stearate, lanolin, magnesium hydroxide, kaolin and water. Alternatively, the medicament may also be formulated a lotion or cream comprising the active components suspended or dissolved in a carrier. Such carriers include, but are not limited to, one or more of mineral oil such as paraffin, vegetable oils such as castor oil, castor seed oil and hydrogenated castor oil, sorbitan monostearat, polysorbat, fatty acid esters such as cetyl ester, wax, fatty acid alcohols such as cetyl alcohol, stearyl alcohol, 2-octyldodecanol, benzyl alcohol, alcohols, triglycerides and water. Alternatively, the medicament may also be formulated with a suitable gel comprising the active components suspended or dissolved in a carrier. Such carriers include, but are not limited to, one or more of water, glycerol, propyleneglycol, liquid paraffin, polyethylene, fatty oils, cellulose derivatives, bentonite and colloidal silicon dioxide.

It is to be understood that the formulation of a medicament preferably takes place under GMP standardized conditions in order to ensure quality, pharmaceutical security, and effectiveness of the medicament. Further criteria for an ingredient being pharmaceutically acceptable can be derived from approval regulations by a regulatory agency or other generally recognized pharmacopoeias.

The medicament referred to herein is, preferably, administered topically. However, a systemic administration is also feasible. For systemic administration, the medicament can be applied intra-muscular, subcutaneous or intravenous. Other routes of administration are, however, also possible.

The medicament shall, preferably, provide to a subject in need thereof a therapeutically effective dose of the peptide of the invention. A therapeutically or prophylactically effective dose refers to an amount of the peptide which in a subject in need thereof prevents, ameliorates or treats the symptoms accompanying a disease or condition referred to in this specification. Therapeutic or prophylactic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. A therapeutically or prophylactically effective dose can be provided at once, i.e., as a single bolus or by repeated administration of the medicament. The dosages are, preferably, given once a week, more preferably 2 times, 3 times, 4 times, 5 times or 6 times a week and most preferably daily and even more preferably, 2 times a day or more often.

The dosage regimen for the medicament referred to herein will be determined by an attending physician and clinical factors. As is well known in the medical arts, dosages for an individual depend upon many factors, including the patient's size, body surface area, age, the particular compound to be administered, sex, time and route of administration, general health, and other drugs being administered concurrently. Dosage recommendations shall be indicated in the prescribers or users instructions in order to anticipate dose adjustments depending on the considered recipient.

Preferably, the medicament is administered directly or in combination with an adjuvant. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. These compounds are added in conditions respecting pH limitations.

The present invention in particular provides a pharmaceutical composition comprising the peptide of the invention and, preferably, one or more pharmaceutically acceptable carriers or excipients. Preferably, said composition comprises the peptide in a concentration of from 0.01 to 100 mg/ml, preferably of from 0.05 to 50 mg/ml, more preferably of from 0.1 to 10 mg/ml, more preferably of from 0.2 to 5 mg/ml, and even more preferably of from 0.5 to 2 mg/ml.

It has been found in the studies underlying the present invention that the peptide of the invention effectively inhibits the secretion of pro-inflammatory substances, preferably of pro-inflammatory cytokines, more preferably of Interleukin-1 (IL-1), and even more preferably of Interleukin-1 alpha (IL1-alpha). Preferably, the secretion of such pro-inflammatory substances is inhibited in epithelial cells and, in particular, in the keratinocytes of the skin.

Accordingly, the peptide or pharmaceutical composition of the invention is to be used, preferably, as a medicament for the treatment and/or prophylaxis of inflammation of epithelial tissues, allergies, allergic reactions, rash, and/or rheumatoid arthritis, more preferably for the treatment and/or prophylaxis of inflammation, allergies, and/or allergic reactions of the epidermis, more preferably for the treatment and/or prophylaxis of dermatitis, and even more preferably for treatment and/or prophylaxis of atopic dermatitis, seborrhoeic dermatitis, psoriasis, poison-ivy dermatitis, eczema herpeticum, kerion, diaper rash, or scabies.

The aforementioned diseases and disorders are well known to the skilled artisan and the symptoms and clinical parameters accompanying them are described in standard textbooks of medicine such as Stedman or Pschyrembl.

The term "treatment" as used herein refers to ameliorating the symptoms and/or clinical parameters accompanying a disease or disorder referred to above in a statistically significant portion of the subject to be treated by the medicament and to an extent which becomes apparent in that the improvement of the symptoms or clinical parameters is statistically significant, too. Preferably, the term also encompasses the entire restoration of health in a subject to be treated with respect to the aforementioned diseases or disorders. How to determine whether a statistically significant portion can be successfully treated or whether an improvement of symptoms or clinical parameters is statistically significant can be determined by the skilled person without further ado by applying standard statistics such as Student's t-test and the like.

The term "prophylaxis" as used herein refers to maintaining health with respect to the aforementioned diseases or disorders within a prophylactic time window for a statistically significant portion of subjects to be subjected to the prophylaxis. Maintaining health with respect to the diseases or disorders referred to herein can be assessed by monitoring a subject for the presence or absence of symptoms accompanying the diseases or disorders and/or clinical parameter shifts indicative for the diseases or disorders during the prophylactic time window. Whether a portion is statistically significant can be determined as specified elsewhere herein. Preferred prophylactic time windows as used herein are up to 6 weeks, up to 5 weeks, up to 4 weeks, up to 3 weeks, up to 2 weeks, up to 1 week, up to 2 days, or at least 1 day.

A subject as referred to herein refers to an animal, preferably a mammal, more preferably a human, farming animal, such as a cow, pig, horse, sheep, or goat or a pet, such as a cat or dog. Most preferably, the subject is a human.

The present invention also contemplates following from the above a method for treating of a pro-inflammatory condition or disease in a subject, said method comprising administering to a subject suffering from the aforementioned condition or disease a therapeutically effective dose of the peptide of the invention.

Moreover, contemplated by the present invention is a method for prophylaxis of a pro-inflammatory condition or disease in a subject, said method comprising administering to an apparently healthy subject a prophylactically effective dose of the peptide of the invention.

In a preferred embodiment of these methods referred to above, the pro-inflammatory condition or disease is inflammation of epithelial tissues, allergies, allergic reactions, rash, and/or rheumatoid arthritis, more preferably for the treatment and/or prophylaxis of inflammation, allergies, and/or allergic reactions of the epidermis, more preferably for the treatment and/or prophylaxis of dermatitis, and even more preferably for treatment and/or prophylaxis of atopic dermatitis, seborrhoeic dermatitis, psoriasis, poison-ivy dermatitis, eczema herpeticum, kerion, diaper rash, or scabies.

It will be understood that the methods are, moreover, applicable to both human therapy and veterinary applications.

The present invention, furthermore, contemplates a method for the manufacture of a medicament comprising the step of formulating the peptide of the invention in a pharmaceutically acceptable form.

Details on how the peptide can be formulated in a pharmaceutically acceptable form are described elsewhere herein in detail.

It has been, furthermore, found in accordance with the present invention that the peptide of the invention is capable of affecting the growth of microorganisms which are part of the microflora on skin. Specifically, the growth of pathogenic bacteria was found to be inhibited specifically while normal healthy microorganisms which may be present on skin were stimulated in growth. This effect of the peptide of the invention is a direct effect on the bacteria of the microflora and shall be independent of any effects mediated by the skin of a subject which harbors the said microflora. Thus, by directly affecting the microflora the peptide of the present invention elicits a probiotic effect in that it increases the probiotic bacteria in the microflora at the expense of the pathogenic bacteria. As a consequence, the overall well being and health of a subject will improve due to the generation of a essentially probiotic microflora on the skin.

Therefore, the peptide of the invention is also to be used for inhibiting the growth of transient pathogenic skin microflora, preferably for inhibiting the growth of transient pathogenic skin microflora belonging to the *Staphylococcus* genus, and preferably for inhibiting the growth of *S. aureus*. Further, it is to be used for stimulating the growth of healthy normal resident skin microflora, preferably for stimulating the growth of healthy normal resident skin microflora belonging to the *Staphylococcus* genus, and preferably for stimulating the growth of *S. epidermidis*.

The term "transient pathogenic skin microflora" as used herein refers to microorganisms which are transiently present on the surface of the skin. The presence of said microorganisms on the skin shall be harmful for the subject in that the microorganisms itself elicit pathogenic process in the subject or destroy beneficial microorganism such as microorganisms of a probiotic microflora referred to elsewhere herein. Preferably, the microorganisms are bacteria. More preferably, the said bacteria are of the *Staphylococcus* genus and, even more preferably, *S. aureus*.

The term "healthy normal resident skin microflora" as used herein refers to microorganisms which are resident on the surface of the skin of a subject and which are not harmful for the subject. Preferably, the microorganisms are probiotic microorganisms which protect the subject from pathogenic microorganisms or which actively improve health and well being of the subject. Preferably, the microorganisms are bacteria. More preferably, the said bacteria are of the *Staphylococcus* genus and, even more preferably, *S. epidermidis*.

The term "inhibiting the growth" as used herein refers to a reduction of the growth rate of the bacteria. Preferably, the growth is statistically significant inhibited. Preferably, a reduction of the growth rate envisaged by the present invention is a reduction of at least 20%, at least 30%, at least 40%, at least 50%, at least 75%, at least 80% or at least 90%. The growth rate for bacteria can be determined by the skilled person using methods well known in the art without further ado.

The term "stimulating the growth" refers to an increase in the growth rate. Preferably, said increase is statistically significant. Preferably, a stimulation of growth is characterized by an increase in the growth rate of at least 20%, at least 30%, at least 40%, at least 50%, at least 75%, at least 80%, at least 90% or at least 100%.

The peptide is administered in accordance with the aforementioned uses to the skin of a subject comprising pathogenic skin microflora or suspected to comprise such a microflora. Dosages for the peptide which are effective for inhibiting the growth of pathogenic microflora or which stimulate the growth of healthy normal resident microflora can be determined as described elsewhere herein. Preferably, the peptide is to be administered once a week, more preferably 2 times, 3 times, 4 times, 5 times or 6 times a week and most preferably daily and even more preferably, 2 times a day or more often. In particular, it may be preferable to give a dosage each time after a disturbance of the resident skin flora occurred, e.g. by washing. However, during progression of the treatment the dosages can be given in much longer time intervals and in need can be given in much shorter time intervals, e.g., several times a day. In a preferred case the immune response is monitored using herein described methods and further methods known to those skilled in the art and dosages are optimized, e.g., in time, amount and/or composition. Progress can be monitored by periodic assessment. It is also envisaged that the pharmaceutical compositions are employed in co-therapy approaches, i.e. in co-administration with other medicaments or drugs, for example other drugs for protecting skin against pathogenic microorganisms.

In addition to the aforementioned, the present invention further relates to a cosmetic composition comprising the peptide of the invention. In particular, according to these embodiments of the present invention, the cosmetic composition is provided for non-therapeutic use, wherein it is preferably administered to a subject for cosmetic purposes.

The term "cosmetic composition" as used in accordance with the present invention, relates to one or more compositions which comprise at least one tetrapeptide of the present invention as described above. It is envisaged that the compositions of the present invention which are described herein below comprise the one or more further ingredients to the inventive peptide in any combination. Preferably, the cosmetic compositions of the present invention may comprise at least one further ingredient suitable for stimulating the growth of healthy normal resident skin microflora and/or for protecting the skin against pathogenic microorganisms, and preferably for inhibiting the growth of transient pathogenic skin microflora. According to a particularly preferred embodiment, the term "ingredients suitable for protecting the skin against pathogenic microorganisms" designates compounds or compositions and/or combinations thereof which lower the pH and/or maintain a low pH level of the skin, wherein the term "low pH level of the skin" preferably refers to a pH level of between 6 and 7.

In general, there is no particular restriction as to the amount of inventive peptide which may be contained in the cosmetic composition of the present invention. Thus, by way of example, the cosmetic composition may contain the inventive peptide in a concentration ranging anywhere from 0.005 to 20 mg/ml, wherein according to preferred embodiments, the content thereof ranges 0.01 to 10 mg/ml, preferably from 0.05 to 5 mg/ml, more preferably from 0.1 to 2 mg/ml, and even more preferably from 0.2 to 1 mg/ml. Within the meaning of the present invention the concentration given in mg/ml indicates the content of the inventive peptide in the composition, wherein according to preferred embodiments wherein the peptide is comprised in a larger polypeptide or protein the content is based on the weight of the peptide of the present invention contained therein and not on the weight of the polypeptide or protein in which it is contained.

In addition, the present invention relates to the use of a peptide as described above for the preparation of a cosmetic composition. In particular, the present invention provides a method for the production of a cosmetic composition comprising the steps of formulating a tetrapeptide as described above with one or more cosmetically acceptable carriers or excipients.

Therefore, the present invention also relates to a cosmetic composition which further comprises one or more cosmetically and/or pharmaceutically acceptable carriers or excipients.

In general, the cosmetic compositions of the invention may comprise any further components which are suitable for their cosmetic application. In particular, said compositions may comprise one or more of the aforementioned pharmaceutically acceptable carriers, stabilizers, sustained release agents, emollients, emulsifiers, surfactants, film formers, preservatives, perfumes, waxes, and other ingredients including biological additives to enhance performance or consumer appeal, buffering agents, chelating agents such as EDTA, emulsion stabilizers, pH adjusters, opacifying agents, and propellants, as described in the foregoing with respect to embodiments and preferred embodiments of the medicament and pharmaceutical composition of the present invention.

In addition thereto, the cosmetic composition of the present invention may also comprise further auxiliaries as are customarily used in such preparations such as one or more of antifoams, dyes, pigments, thickeners, surface-active substances, finishing agents, fats, oils, and other customary constituents, of a cosmetic or dermatological formulation, such as alcohols, polyols, polymers, foam stabilizers, solubility promoters, electrolytes, organic acids, organic solvents, or silicone derivatives. According to a particularly preferred embodiment, said compositions are in the form of emulsions, e.g. oil in water or water in oil emulsions, in the form of ointments or in the form of micro-capsules and/or liposomes.

In general, the cosmetic and pharmaceutical compositions may be provided in any form suitable for their respective application. Thus, by way of example, the compositions may be in solid, liquid or gaseous form and may be, inter alia, in the form of (a) powder(s), (a) solution(s) (an) aerosol(s), suspensions, emulsions, liquids, elixirs, extracts, tincture or fluid extracts. According to preferred embodiments, the compositions of the invention are in a form which is suitable for topical administration. Forms suitable for topical application include, a paste, an ointment, a lotion, a cream, a gel or a transdermal patch.

Preferably, the composition of the present invention is a cosmetic composition further comprising a cosmetically acceptable carrier or excipient. More preferably, said cosmetic composition is a paste, an ointment, a lotion, a cream or a gel. In particular, the cosmetic composition of the present invention comprises the inventive peptide in connection with the composition of the invention and further a cosmetically acceptable carrier.

Within the meaning of the present invention, the term "cosmetically acceptable carrier" means any suitable vehicle, which can be used to apply the present compositions to the skin in a safe and effective manner. Such vehicle may include materials such as emulsions, e.g. oil in water or water in oil emulsions, ointments or micro capsules, it is also advantageous to administer the active ingredients in encapsulated form, e.g. as cellulose encapsulation, in gelatine, with polyamides, niosomes, wax matrices, with cyclodextrins or liposomally encapsulated. The term "safe and effective amount" as used herein preferably means a sufficient amount to stimulate growth of at least one microorganism of the resident skin microbial flora.

According to the present invention, a suitable paste as a carrier comprises the inventive peptide suspended in a carrier. Such carriers include, but are not limited to, petroleum, soft white paraffin, yellow petroleum jelly and glycerol.

The cosmetic composition may also be formulated with a suitable ointment comprising the active components suspended or dissolved in a carrier. Such carriers include, but are not limited to, one or more of glycerol, mineral oil, liquid oil, liquid petroleum, white petroleum, yellow petroleum jelly, propylene glycol, alcohols, triglycerides, fatty acid esters such as cetyl ester, polyoxyethylene polyoxypropylene compound, waxes such as white wax and yellow beeswax, fatty acid alcohols such as cetyl alcohol, stearyl alcohol and cetylstearylalcohol, fatty acids such as stearic acid, cetyl stearate, lanolin, magnesium hydroxide, kaolin and water. Alternatively, the cosmetic composition may also be formulated with a suitable lotion or cream comprising the active components suspended or dissolved in a carrier. Such carriers include, but are not limited to, one or more of mineral oil such as paraffin, vegetable oils such as castor oil, castor seed oil and hydrogenated castor oil, sorbitan monostearat, polysorbat, fatty acid esters such as cetyl ester, wax, fatty acid alcohols such as cetyl alcohol, stearyl alcohol, 2-octyldodecanol, benzyl alcohol, alcohols, triglycerides and water. Alternatively, the cosmetic composition may also be formulated with a suitable gel comprising the active components suspended or dissolved in a carrier. Such carriers include, but are not limited to, one or more of water, glycerol, propyleneglycol, liquid paraffin, polyethylene, fatty oils, cellulose derivatives, bentonite and colloidal silicon dioxide.

According to preferred embodiments, the cosmetic composition further comprises emollients. Emollients may be used in amounts which are effective to prevent or relieve dryness. More preferably, emollients used in the cosmetic compositions of the present invention include one or more of hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; phospholipids; sterols; and amides.

Thus, preferred emollients include mineral oil, especially mineral oils having a viscosity in the range of 50 to 500 SUS (Saybolt Universal Second), lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purcellin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12-C15) alcohols, the octanoates and decanoates of alcohols and polyalcohols such as those of glycol and glycerol, and ricinoleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

According to further preferred embodiments, the cosmetic composition according to the invention comprises one or more emulsifiers. In particular, the emulsifiers (i.e., emulsifying agents) are preferably used in amounts effective to provide uniform blending of ingredients of the composition. Preferred emulsifiers include one or more of (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl surfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate; and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol. The selection of emulsifiers is exemplarily described in Schrader, Grundlagen and Rezepturen der Kosmetika, Hüthig Buch Verlag, Heidelberg, $2^{nd}$ edition, 1989, $3^{rd}$ part.

According to further preferred embodiments of the present invention, the cosmetic composition comprises a surfactant. Suitable surfactants include, for example, those surfactants generally grouped as cleansing agents, emulsifying agents, foam boosters, hydrotropes, solubilizing agents, suspending agents and nonsurfactants (facilitates the dispersion of solids in liquids).

In general, surfactants are usually classified as amphoteric, anionic, cationic and nonionic surfactants, wherein one or more of said classes of surfactants are preferably used in the cosmetic composition of the invention. In particular, preferred amphoteric surfactants include one or more acylamino acids and derivatives and N-alkylamino acids. Furthermore, preferred anionic surfactants include one or more of the following: acylamino acids and salts, such as, acylglutamates, acylpeptides, acylsarcosinates, and acyltaurates; carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Furthermore, preferred cationic surfactants include one or more of the following: alkylamines, alkyl imidazolines, ethoxylated amines, and quaternaries (such as, alkylbenzyldimethylammonium salts, alkyl betaines, heterocyclic ammonium salts, and tetra alkylammonium salts). In addition to these, preferred nonionic surfactants include one or more of the following: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

Furthermore, a cosmetic composition is preferred according to the invention which comprises a film former. In general, film formers which are used in accord with the invention preferably keep the composition smooth and even. According to the present invention, preferred film formers include one or more of the following: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; and acryliclacrylate copolymer.

Generally, the film formers can be used in any suitable amount. By way of example, the film formers may be used in the inventive cosmetic composition in amounts ranging anywhere from 0.1% to 10% by weight of the total composition, wherein preferably 1% to 8% are contained therein, more preferably 0.1% to 5%. According to further preferred embodiments, one or more humectants are comprised in the inventive cosmetic composition, wherein said humectants are preferably selected from the group consisting of fructose; glucose; glulamic acid; glycerin; honey; maltitol; methyl gluceth-10; methyl gluceth-20; propylene glycol; sodium lactate; sucrose; and combinations thereof.

It is further preferred according to the invention that the cosmetic composition comprises one or more preservatives. More preferably, the one or more preservatives comprise one or more of butylparaben; ethylparaben; imidazolidinyl urea; methylparaben; O-phenylphenol; propylparaben; quaternium-14; quaternium-15; sodium dehydroacetate; and zinc pyrithione.

In general, the preservatives may be used in any amount which is effective to prevent or retard microbial growth. Preferably, the preservatives are used in an amount ranging from 0.1% to 1% by weight of the total composition, more preferably from 0.1% to 0.8% by weight, and even more preferably from 0.1% to 0.5% by weight.

The cosmetic composition according to the invention may also further comprise a perfume. Perfumes (fragrance components) and colorants (coloring agents) well known to those skilled in the art may be used in effective amounts to impart the desired fragrance and color to the compositions of the invention.

According to embodiments of the present invention which are further preferred, the cosmetic composition comprises one or more waxes. Preferred waxes include one or more of the following: animal waxes, such as beeswax, and preferably hexadecanoic acid ester of tricontanol contained therein, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Alternatively or in addition to these, one or more synthetic waxes may be used in the cosmetic composition, wherein said one or more synthetic waxes preferably include polyethylene, polyoxyethylene, and hydrocarbon waxes derived from carbon monoxide and hydrogen, and combinations of two or more thereof.

In particular, preferred waxes which may be used in the cosmetic composition of the present invention include one or more of cerosin; cetyl esters; hydrogenated jojoba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sulfurized jojoba oil; synthetic beeswax; synthetic jojoba oils; trihydroxystearin; cetyl alcohol; stearyl alcohol; cocoa butter; fatty acids of lanolin; mono-, di- and triglycerides which are solid at 25° C., e.g., glyceryl tribehenate (a triester of behenic acid and glycerine) and C19-C36 acid triglyceride (a mixture of triesters of C19-C36 carboxylic acids and glycerine) available from Croda, Inc., New York, N.Y. under the tradenames Syncrowax HRC and Syncrowax HGL-C, respectively; fatty esters which are solid at 25° C.; silicone waxes such as methyloctadecaneoxypolysiloxane and poly(dimethylsiloxy) stearoxysiloxane; stearyl mono- and diethanolamide; rosin and its derivatives such as the abietates of glycol and glycerol; hydrogenated oils solid at 25° C.; and sucroglycerides.

Furthermore, cosmetic compositions are preferred according to the present invention which comprise one or more thickeners (viscosity control agents). Preferred thickeners used in cosmetic compositions of the present invention which are in the form of a solution comprise one or more of algin; carbomers such as carbomer 934, 934P, 940 and 941; cellulose gum; cetearyl alcohol, cocamide DEA, dextrin; gelatin; hydroxyethylcellulose; hydroxypropylcellulose; hydroxypropyl methylcellulose; magnesium aluminum silicate; myristyl alcohol; oat flour; oleamide DEA; oleyl alcohol; PEG-7M; PEG-14M; PEG-9OM; stearamide DEA; stearamide MEA; stearyl alcohol; tragacanth gum; wheat starch; xanthan gum; wherein DEA is diethanolamine, and MEA is monoethanolamine. Alternatively or in addition thereto, thickeners used in cosmetic compositions of the present invention which are in the form of a nonaqueous system preferably comprise one or more of aluminum stearates; beeswax; candelilla wax; carnauba; ceresin; cetearyl alcohol; cetyl alcohol; cholesterol; hydrated silica; hydrogenated castor oil; hydrogenated cottonseed oil; hydrogenated soybean oil; hydrogenated tallow glyceride; hydrogenated vegetable oil; hydroxypropyl cellulose; lanolin alcohol; myristyl alcohol; octytdodecyl stearoyl sulfate; coleyl alcohol; ozokerite; microcystalline wax; paraffin, pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like. Furthermore, it is preferred according to the present invention that the cosmetic composition comprises customary native and synthetic thickeners or gel formers in formulations which preferably comprise one or more crosslinked polyacrylic acids and derivatives thereof, polysaccharides, such as xanthane gum or alginates, carboxymethylcellulose or hydroxycarboxymethylcellulose, hydrocolloids such as gum Arabic or montmorillonite minerals, such as bentonites or fatty alcohols, polyvinyl alcohol and polyvinlypyrrolidone, and combinations of two or more thereof.

Other ingredients which are preferably comprised in the inventive cosmetic composition include one or more of biological additives to enhance performance or consumer appeal such as amino acids, proteins, vanilla, aloe extract, bioflavinoids, and the like; buffering agents, chelating agents such as EDTA; emulsion stabilizers; pH adjusters; opacifying agents; and propellants such as butane carbon dioxide, ethane, hydrochlorofluorocarbons 22 and 142b, hydrofluorocarbon 152a, isobutane, isopentane, nitrogen, nitrous oxide, pentane, propane, and the like.

Alternatively or in addition to these, the cosmetic compositions of the present invention preferably further comprise one or more compounds which have an antioxidative, free-radical scavenger, skin moisturizing or moisture-retaining, antierythematous, antiinflammatory, and/or antiallergic action, in order to supplement or enhance their cosmetic action by non-therapeutic means. According to preferred embodiments thereof, said compounds comprise one or more of vitamins, plant extracts, alpha- and beta-hydroxy acids, ceramides, antiinflammatory, antimicrobial or UV-filtering substances, including derivatives and mixtures thereof. Furthermore, the cosmetic compositions of the present invention preferably further comprise one or more substance which absorb UV radiation in the UV-B and/or UV-A region. In embodiments of the invention wherein the cosmetic composition further comprises one or more of the aforementioned compounds, it is further preferred that the composition comprises a lipid phase, wherein said lipid phase preferably comprises one or more substances selected from the group consisting of mineral oils, mineral waxes, branched and/or unbranched hydrocarbons and hydrocarbon waxes, triglycerides of saturated and/or unsaturated, branched and/or unbranched C8-C24-alkanecarboxylic acids, and combinations of two or more thereof, wherein the oils include synthetic, semisynthetic as well as natural oils. More specifically, the lipid phase of the cosmetic composition according to said embodiments preferably comprises one or more components selected from the group consisting of olive oil, palm oil, almond oil; fats or waxes, esters of saturated and/or unsaturated, branched and/or unbranched C3-C30-alkane carboxylic acids and saturated and/or unsaturated, branched and/or unbranched C3-C30-alcohols, from aromatic carboxylic acids and saturated and/or unsaturated, branched and/or unbranched C3-C30-alcohols, for example isopropyl myristate, isopropyl stearate, hexyldecyl stearate, oleyl oleate; and also synthetic, semisynthetic and natural mixtures of such esters, such as jojoba oil, alkyl benzoates or silicone oils, such as, for example, cyclomethicone, dimethylpolysiloxane, diethylpolysiloxane, octamethylcyclo-tetrasiloxane and mixtures thereof or dialkyl ethers.

In general, the cosmetic compositions of the invention may be formulated and provided in any suitable form which is advantageous and effective for consumer use. In this respect, considering the advantageous effects of the inventive peptide and compositions containing the same, in particular in non-therapeutic cosmetic applications, it is preferred that inventive peptide and cosmetic compositions containing the same be formulated as or contained in compositions for the cleansing of the skin, such as bar soaps, toilet soaps, curd soaps, transparent soaps, luxury soaps, deodorizing soaps, cream soaps, baby soaps, skin protection soaps, abrasive soaps, syndets, liquid soaps, pasty soaps, soft soaps, washing pastes, liquid washing, showering and bath preparations, e.g. washing lotions, shower preparations, shower gels, foam baths, cream foam baths, oil baths, bath extracts, scrub preparations, in-situ products, shaving foams, shaving lotions, shaving creams. In addition, they are suitable for skin cosmetic preparations, such as W/O or O/W skin and body creams, day and night creams, light protection compositions, aftersun products, hand care products, face creams, multiple emulsions, gelees, microemulsions, liposome preparations, niosome preparations, antiwrinkle creams, face oils, lipogels, sportgels, moisturizing creams, bleaching creams, vitamin creams, skin lotions, care lotions, ampoules, aftershave lotions, preshaves, humectant lotions, tanning lotions, cellulite creams, depigmentation compositions, massage preparations, body powders, face tonics, deodorants, antiperspirants, nose strips, antiacne compositions, repellents and others.

Therefore, according to preferred embodiments of the present invention, the inventive peptide or the inventive cosmetic and/or pharmaceutical composition comprising the same is contained in a cleansing agent and/or formulation for application to the epidermis, preferably to the facial skin and/or to the scalp, and even more preferably to the facial skin,
wherein the cleansing agent is preferably a soap and/or lotion, more preferably a facial lotion and/or a shampoo, and
wherein the formulation for application to the epidermis is preferably a liquid or semisolid solution, lotion, cream, gel, or ointment.

According to preferred embodiments of the present invention wherein the peptide or a composition comprising the same is for topical application, the peptide or composition is preferably formulated with a suitable paste, ointment, lotion, cream, gel or as a transdermal patch. Depending on the field of use, however, the means of application may preferably be in the form of a spray (pump spray or aerosol), foam, gel spray, mousse, suspensions or powders. According to the aforementioned formulations and modes of applications it therefore preferable that the cosmetic and or pharmaceutical composition comprises a suitable propellant for the aforementioned types of formulations, and in particular with respect to modes of application involving an aerosol. In general, any conceivable propellant may be comprised in said specific cosmetic and pharmaceutical composition, wherein according to the invention the use of a propellant comprising one or more of propane, butane, pentane, and mixtures thereof is preferred.

Therefore, according to certain embodiments of the inventive peptide or the inventive cosmetic and/or pharmaceutical composition comprising the same, it is further preferred that the cleansing agent and/or formulation for application to the epidermis is contained in and/or applied as an aerosol.

The present invention further concerns the use of the inventive peptide for non-therapeutic skin care. In particular, the present invention further concerns the use of the inventive peptide or of a composition comprising the same for the treatment and/or prophylaxis of a dry skin condition. Within the meaning of the present invention, the term "dry skin condition" generally designates any condition of the epidermis for which increasing or maintaining the moisture content thereof is beneficial to its cosmetic appearance and/or to the well-being of the subject to which the inventive peptide or composition is applied. In particular, the term does not designate a pathological condition of the skin necessitating therapeutic action.

The term "skin", on the other hand, generally refers to the body's outer covering, as known to the person skilled in the art. Preferably the term relates to three layers: epidermis, dermis, and subcutaneous fatty tissue. The epidermis is the outermost layer of the skin. It typically forms the waterproof, protective wrap over the body's surface and is made up of stratified squamous epithelium with an underlying basal lamina. It usually contains no blood vessels, and is nourished by diffusion from the dermis. The main types of cells which make up the epidermis are keratinocytes, with melanocytes and Langerhans cells also present. The epidermis is divided into several layers where cells are formed through mitosis at the innermost layers. They move up the strata changing shape and composition as they differentiate and become filled with keratin. They eventually reach the top layer called stratum corneum and become sloughed off, or desquamated. The outermost layer of the epidermis consists of 25 to 30 layers of dead cells. Conventionally, the epidermis is divided into 5 sublayers or strata (from superficial to deep): the stratum corneum, the stratum lucidum, the stratum granulosum, the stratum spinosum and the stratum germinativum or stratum basale. Typically, the interface between the epidermis and dermis is irregular and consists of a succession of papillae, or fingerlike projections, which are smallest where the skin is thin and longest in the skin of the palms and soles. Typically, the papillae of the palms and soles are associated with elevations of the epidermis, which produce ridges. Subcutaneous fatty tissue is the deepest layer of the skin. A characteristic of this layer is that it is composed of connective tissue, blood vessels, and fat cells. Typically, this layer binds the skin to underlying structures, insulates the body from cold, and stores energy in the form of fat. In general the skin forms a protective barrier against the action of physical, chemical, and bacterial agents on the deeper tissues. This means that tissues belonging, e.g. to the oral cavity or the vaginal region or mucous membranes do not belong to the skin. In a preferred embodiment the term "skin" relates to the outermost layer of the body's covering, i.e. the epidermis. In a more preferred embodiment the term "skin" relates to the stratum corneum of the epidermis. In an even more preferred embodiment the term skin relates to the outermost 25 to 30 layers of dead cells of the epidermis. In the most preferred embodiment the term "skin" relates to the outermost 10 layers of dead cell of the epidermis.

In principle, there is no restriction according to the present invention as to the regions of the skin which may be subject to skin-care using the inventive peptide or composition comprising the same. Preferably, however, the inventive peptide and composition is preferably used for skin-care of those regions of the skin which are prone to a dry-skin condition. More preferably, the skin-care is directed to those regions of the skin which may easily become dry as a result of predisposition to dryness and/or environmental and seasonal factors and/or general hygiene involving the frequent washing of those regions of the skin. Thus, according to preferred embodiments of the present invention, the inventive protein or composition is employed for the skin-care of the hands, of the facial skin, and/or of the scalp, more preferably of the hands and/or of the facial skin, and even more preferably of the facial skin. According to certain embodiments of the present invention which are preferred, the inventive protein or composition is specifically used for skin-care of the hands and/or lips, more preferably for the skin-care of the lips.

Therefore, the present invention further relates to the use of the inventive peptide or of the inventive composition comprising the same for non-therapeutic skin care, preferably for the treatment and/or prophylaxis of dry skin condition, preferably dry facial skin and/or dry scalp, and even more preferably dry facial skin.

According to further embodiments of the present invention, the inventive peptide or composition comprising the same is used for improving and sustaining the healthy normal resident microflora present on the skin, preferably the healthy normal resident microflora present on the facial skin and/or scalp, and more preferably the healthy normal resident microflora present on the facial skin. In particular, according to said embodiments and preferred embodiments, the inventive peptide or composition is used for stimulating the growth of healthy microflora which normally resident on the skin. In general, with respect to said embodiments and preferred embodiments of the present invention, there is no particular restriction as to the specific components of the healthy normal resident skin microflora which may be stimulated by the inventive protein or composition comprising the same, provided that the overall healthy normal resident skin microflora is improved or sustained. According to preferred embodiments thereof, the components of the healthy normal resident skin microflora of which the growth is stimulated comprises healthy normal resident skin microflora belonging to the *Staphylococcus* genus, wherein more preferably the growth *S. epidermidis* is stimulated.

Generally speaking, many different microorganisms exist on the skin. Some belong to the normal (resident) flora of the skin and are harmless commensals and some are potential pathogens.

More specifically, organisms on the skin can be classified into two categories:
1. Resident organisms: resident organisms are permanent inhabitants of the skin which colonise on the surface of the skin, the stratum corneum and within the outer layer of the epidermis and the deeper crevices of the skin and hair follicles. These microorganisms of the resident microbial skin flora can grow and multiply on the skin without invading or damaging the skin tissue. Washing does not easily remove these organisms in deeper skin regions. Resident microorganisms are harmless commensals.
2. Transient organisms: transient organisms are microorganisms which are deposited on the skin but do not multiply there or contaminants which multiply on the skin and persist for short periods. They cannot settle permanently on healthy skin whose microenvironment is heavily determined by the resident micro flora. Transient organisms are potentially pathogenic.

Thus, the term "resident skin microbial flora" relates to the microorganisms which can normally be found on healthy skin, preferably human skin, and which constitute the majority of the microorganisms found on the skin. In particular, the term "resident skin microbial flora" relates to microorganisms which are permanent inhabitants on the surface of the skin, the stratum corneum and within the outer layer of the epidermis and the deeper crevices of the skin and hair follicles. These microorganisms are characterized in that they can grow and multiply on the skin without invading or damaging the skin tissue. A characteristic of these microorganisms is that washing does not easily remove them in deeper skin regions. The microorganisms of the resident skin microbial flora are harmless commensals.

More specifically, the term "resident skin microbial flora" preferably relates to a flora of aerobic and anaerobic microorganisms which can be found on skin, preferably human skin. More preferably, it relates to a flora of microorganisms which comprises *Staphylococcus epidermidis* (coagulase negative), *Micrococcus* spec, Diphteroids and propioni bacteria. Typically, about 90% of the aerobic resident microbial skin flora consists of *Staphylococcus epidermidis*. The remaining about 10% are composed of mainly *Micrococcus* spec. (80% *Micrococcus luteus*) and Diphteroids (13%). The term "Diphtheroid" denotes a wide range of bacteria belonging to the genus *Corynebacterium*. For convenience, cutaneous diphtheroids have been categorized into the following four groups: lipophilic or nonlipophilic diphtheroids; anaerobic diphtheroids; diphtheroids producing porphyrins. Major representatives (90%) of the anaerobic microbial skin flora are propionibacteria; especially *Propionibacterium acnes*, *P. granulosum* and *P. avidum* can be isolated from the skin. The anaerobic flora accounts for approximately 4% of the total resident skin flora.

More preferably, more than 90% of the microorganisms of the microbial flora belong to *Staphylococcus epidermidis*, *Micrococcus* spec, Diphteroids and propioni bacteria. Even more preferably, the healthy resident skin microbial flora is characterized in that its major constituent is *Staphylococcus epidermidis*.

The term "stimulates" in connection with the growth of microorganisms of the resident skin microbial flora means that the growth of one or more of these microorganisms is increased when contacted with a peptide or composition according to the invention. An increased growth means preferably an increase in proliferation, i.e. cell divisions per time unit. Alternatively, the term "stimulates" also refers to an increase in size of individual cells. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode. Accordingly, within the meaning of the present invention, an increased growth preferably means an increase in biomass production per time unit.

The stimulation of growth of the microorganism(s) of the resident skin microbial flora can be determined by any suitable means known in the art, wherein the stimulation is preferably observed in vitro, more preferably in an assay in which a peptide or composition according to the invention is contacted with one or more microorganisms of the resident skin microbial flora and the growth of the(se) microorganism(s) of the resident skin microbial flora is determined. The growth can be determined by counting the numbers of cells/colonies after different time intervals of incubation and can be compared with a control which does not contain a microorganism according to the invention, thereby allowing to determine whether there is an increase in growth. The determination of the growth may be effected by available means and methods for determining the number of cells and/or colonies, such as by staining with an appropriate dye and/or optical means such as densitometry and counting the cells/colonies under the microscope.

Preferably, the stimulation of growth of the microorganism(s) of the resident skin microbial flora is determined using in an in situ skin assay. By way of example, an in situ skin assay may be conceived to comprise the following steps: cultivation of at least one microorganism of the resident skin microbial flora and evenly spreading it on an area of skin of a test individual; applying an aliquot of a peptide or composition according to the invention in a punctual area within the area on which the microorganism(s) of the resident skin microbial flora has/have been spread; incubating the skin for an amount of time sufficient to allow growth of the microorganism(s) of the resident skin microbial flora; transferring the upper skin layers, including the microorganisms comprised in these, to an agar plate containing an appropriate growth medium; incubation of the agar plates for a period of time and under conditions allowing the growth of the microorganism(s) of the resident skin microbial flora; determining the growth of the microorganism(s) of the resident skin microbial flora surrounding the area at which the peptide or composition according to the invention was applied and comparing it to the growth of the microorganism(s) in a control in which no peptide of the invention was applied.

The area of skin used for this assay may be any suitable area of skin of an individual, preferably of a human individual. In a preferred embodiment it is an area of skin on the forearm of a human individual. The size of the area of the skin used for testing preferably preferably ranges from 1 to 40 cm$^2$, more preferably from 5 to 20 cm$^2$, even more preferably from 5 to 10 cm$^2$.

According to an exemplary mode of conducting the in situ skin assay, microorganism(s) of the resident skin microbial flora are evenly distributed on the area, preferably in a density of approximately 10$^2$ cfu/cm$^2$-10$^3$ cfu/cm$^2$. The microorganism(s) spread on the skin are air dried and an aliquot of a peptide or composition according to the invention is applied in a punctual manner within the area. This can be achieved by means known to the person skilled in the art.

The subsequent incubation of the skin preferably takes place at room temperature for, e.g., two hours. The transfer of the upper skin layers, including the microorganisms comprised therein, may, e.g., be effected with the help of an adhesive tape stripe. The agar plates to which the upper skin layers have been transferred are incubated at a temperature allowing growth of the microorganism(s) or the resident skin microbial flora to be tested and contain a growth medium known to support growth of this (these) microorganism(s). The incubation typically takes place for about 24 hours. The growth of the microorganism(s) can be detected by methods known to the person skilled in the art. Preferably, it is determined by densitometry or by counting the colonies formed in the neighborhood of the point at which an aliquot of the peptide or composition of the invention was applied. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode.

According to the present invention, the inventive peptide or a composition comprising the same is preferably regarded to stimulate the growth of one or more microorganisms of the resident skin microbial flora if it leads to an increase of growth of at least one such microorganism in an in vitro hole plate assay of at least 5%, preferably of at least 10%, 20%, 30%, 40%, 50%, 60%, or 70%, more preferably of at least 75% and more preferably of at least 80% and even more preferably of at least 85% in comparison to a control to which no inventive peptide or composition comprising the same has been added. More preferably, the inventive peptide or a composition comprising the same is regarded as stimulating the growth of one or more microorganisms of the resident skin microbial flora if it leads to an increase of growth of at least one such microorganism in an in situ skin assay of at least 5%, preferably of at least 10%, 20%, 30%, 40%, 50%, 60%, or 70%, more preferably of at least 75%, even more preferably of at least 80% and most preferably of at least 85%.

According to a preferred embodiment of the presenting invention, in addition to stimulating the growth of *S. epidermidis*, the peptide or composition of the present invention also stimulates the growth of *Micrococcus* spec, preferably of *Micrococcus luteus*. In a further preferred embodiment, also the growth of Diphteroids, preferably of bacteria belonging to the genus *Corynebacterium* is stimulated. In a particularly preferred embodiment the peptide according to the invention stimulates the growth of the majority of the microorganisms of the resident skin microbial flora, preferably 60% or more of the healthy normal resident skin microflora population, more preferably 70% or more, more preferably 80% or more, more preferably 90% or more, and even more preferably 95% or more.

Furthermore, according to the embodiments and preferred embodiments of the present invention relating to the use of the inventive peptide or composition for stimulating the growth of healthy normal resident skin microflora, it is further preferred that said use does not additionally stimulate the growth of transient pathogenic microorganisms. In general, there is no particular restriction as to the specific types of transient pathogenic microorganisms of which the growth is not additionally stimulated by the use of the inventive peptide or composition, provided that the overall healthy normal resident skin microflora is improved or sustained. It is, however, preferred that the transient pathogenic microorganisms of which the growth is not additionally stimulated comprises *S. aureus*. Within the meaning of the present invention, the growth of a microorganism is not stimulated by the inventive peptide or composition if no stimulation of its growth may be detected when compared to a control sample not containing the inventive peptide or composition.

Therefore, the present invention further relates to the use of the inventive peptide or of the inventive composition comprising the same for stimulating the growth of healthy normal resident skin microflora, preferably for stimulating the growth of healthy normal resident skin microflora belonging to the *Staphylococcus* genus, more preferably for stimulating the growth of *S. epidermidis*, and even more preferably for stimulating the growth of *S. epidermidis* without stimulating the growth of transient pathogenic microorganisms, in particular of *S. aureus*.

According to yet further embodiments of the present invention, the inventive peptide or composition comprising the same is used for inhibiting the growth or transient pathogenic skin microflora.

Within the meaning of the present invention, the inventive peptide or a composition comprising the same is regarded as inhibiting the growth of a microorganism of the transient pathogenic skin micro flora if it leads to a decrease of growth of such a microorganism of the transient pathogenic skin micro flora when contacted with it. The term "inhibits the growth of microorganisms of the transient pathogenic skin micro flora" preferably means that the peptide or composition of the invention decreases the growth of at least one, preferably of more than one, preferably of more than two, more preferably of more than five and particularly preferred of any of the microorganisms of the transient pathogenic flora. In a further preferred embodiment, the peptide or composition of the present invention inhibits the growth of the major representative of the transient pathogenic skin micro flora, i.e. *Staphylococcus aureus*. In a further preferred embodiment, the peptide of the present invention specifically inhibits the growth of *Staphylococcus aureus*. "Specifically" preferably means that it inhibits the growth of *Staphylococcus aureus*, but does not significantly or only to a minor degree inhibit the growth of other microorganisms, in particular of those microorganisms which belong to the resident skin micro flora. More preferably, the term "specifically" means that the degree of inhibition on *Staphylococcus* is much higher than the degree of inhibition on another microorganism, in particular a microorganism of the resident skin micro flora. Particularly preferably, the term "specifically" means that in a suitable growth assay known to the person skilled in the art the proliferation of *Staphylococcus aureus* in the presence of the peptide or composition of the present invention is at the most 50% of the proliferation of another microorganism, in particular another microorganism of the resident skin micro flora in the presence of the peptide or composition of the present invention. Preferably, the proliferation of *Staphylococcus aureus* is 40% or less, 30% or less, 20% or less, 10% or less, more preferably 5% or less and most preferably 1% or less of the proliferation of another microorganism, in particular another microorganism of the resident skin micro flora, in the presence of a peptide or composition of the present invention. In a preferred embodiment the peptide or composition of the present invention inhibits the growth of *Staphylococcus aureus* but does not inhibit the growth of *Micrococcus luteus* and/or *Escherichia coli*. According to a particularly preferred embodiment, the specific inhibition of *Staphylococcus aureus* can be detected when culture conditions are used which include glycerol.

Furthermore, a decreased growth means preferably a decrease in proliferation, i.e. in cell divisions per unit. Alternatively, the term "inhibits" preferably refers to a decrease in size of individual cells. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode. A decreased growth thus means a decrease in biomass production per time unit.

The stimulation of growth of the microorganism(s) of the transient pathogenic skin micro flora can be determined by any suitable means known in the art, wherein the stimulation is preferably observed in vitro, more preferably in an assay in which one or more microorganisms of the transient pathogenic skin micro flora is contacted with a peptide or composition according to the invention and the growth of the(se) microorganism(s) of the transient pathogenic skin micro flora is determined. The growth can be determined by counting the numbers of cells/colonies after different time intervals of incubation and can be compared with a control which does not contain a peptide or composition according to the invention, thereby allowing to determine whether there is an increase or decrease in growth. More preferably, the inhibition of growth of the microorganism(s) of the transient pathogenic skin micro flora can be determined in an "in vitro liquid assay". By way of example, such an assay is described in Examples 2 and 3 below.

Even more preferably, the inhibition of growth of the microorganism(s) of the transient pathogenic skin micro flora can also be observed in an "in situ skin assay". In particular, said assay corresponds to the "in situ skin assay" described in the foregoing with respect to the monitoring of the stimulation of the growth of the microorganism(s) of the resident skin microbial flora, with the difference that the agar plates to which the upper skin layers have been transferred are incubated at a temperature allowing growth of the microorganism(s) or the transient pathogenic skin micro flora to be tested and contain a growth medium known to support growth of this (these) microorganism(s).

According to the present invention, the inventive peptide or a composition comprising the same is preferably regarded to inhibit the growth of one or more microorganisms of the pathogenic transient micro flora if it leads to a decrease of growth of at least one such microorganism in an "in vitro hole plate assay" of at least 5%, preferably of at least 10%, 20%, 30%, 40%, 50%, 60%, or 70%, 80%, more preferably of at least 90% and more preferably of at least 95% and even more preferably of at least 99% in comparison to a control to which no inventive peptide or composition comprising the same has been added. More preferably, the inventive peptide or a composition comprising the same is regarded to inhibit the growth of one or more microorganisms of the pathogenic transient micro flora if it leads to a decrease of growth of at least one such microorganism in an "in vitro liquid assay" of at least 5%, preferably of at least 10%, 20%, 30%, 40%, 50%, 60%, or 70%, 80%, more preferably of at least 90% more preferably of at least 95% and even more preferably of at least 99% in comparison to the control. Even more preferably, a peptide or composition of the invention is regarded as inhibiting the growth of one or more microorganisms of the transient pathogenic skin micro flora if it leads to an decrease of growth of at least one such microorganism in an in situ skin assay of at least 5%, preferably of at least 10%, 20%, 30%, 40%, 50%, 60%, or 70%, 80%, more preferably of at least 90%, more preferably of at least 95% and even more preferably of at least 99%.

Furthermore, according to the embodiments and preferred embodiments of the present invention relating to the use of the inventive peptide or composition for inhibiting the growth of transient pathogenic skin microflora, it is further preferred that said use does not also inhibit the growth of microorganisms which are beneficial, in particular which are beneficial to the skin, and in particular does not inhibit the growth of the healthy normal resident skin micro flora. In general, there is no particular restriction as to the specific types of beneficial microorganisms of which the growth is not equally inhibited by the use of the inventive peptide or composition.

The term "not inhibit" in connection with the growth of beneficial microorganisms, and in particular microorganisms of the resident skin micro flora preferably means that the growth of at least one, preferably of more than one, preferably of more than two, more preferably of more than five and particularly preferred of any of said beneficial microorganisms preferably belonging to the resident skin micro flora is not altered when contacted with a peptide or composition according to the invention. A not altered growth means preferably an unchanged proliferation, i.e. cell divisions per time unit. A peptide or composition of the invention is thus regarded as not altering the growth of a microorganism of the resident skin micro flora if it does not lead to a decreased growth of such a microorganism of the resident skin micro flora when contacted with it. The inhibition of growth or its absence can be tested in vitro or in situ as described above in connection with the property of a peptide or composition of the invention to inhibit the growth of at least one microorganism of the transient pathogenic skin micro flora. Most preferably the test for determining inhibition or its absence takes place by carrying out an "in vitro hole plate assay" and/or "in vitro liquid assay" and/or an "in situ skin assay", preferably with a microorganism of the resident skin micro flora as explained herein.

Alternatively, a peptide or composition of the invention is regarded as not altering the growth of beneficial microorganisms preferably belonging the resident skin micro flora if the growth of the latter microorganism is not decreased or only slightly decreased when contacted with the former peptide or composition of the invention. "Slightly decreased" preferably means that the growth is decreased not more than by 5% when compared to the control, more preferably not more than 2% when compared to the control. The term "not decreased" means that no statistically relevant difference can be found between the growth of the microorganism of the resident skin micro flora contacted with a peptide or composition of the invention when compared to the control where no peptide or composition of the invention is present. The term "not decreased" in a preferred embodiment also includes those cases where a peptide actually leads to an increase of the growth of a microorganism of the resident skin micro flora, i.e. where it stimulates the growth of such a microorganism.

According to particularly preferred embodiments, the beneficial microorganisms of which the growth is not additionally inhibited comprise one or more of the microorganisms constituting the healthy normal resident skin microflora, wherein said one or more microorganisms preferably comprise *S. epidermidis*.

Therefore, the present invention further relates to the use of the inventive peptide or of the inventive composition comprising the same for inhibiting the growth of transient pathogenic skin microflora, preferably for inhibiting the growth of transient pathogenic skin microflora belonging to the *Staphylococcus* genus, more preferably for inhibiting the growth of *S. aureus*, and even more preferably for inhibiting the growth of *S. aureus* without inhibiting the growth of beneficial microorganisms, in particular of *S. epidermidis*.

The present invention is illustrated by the figures and examples as described hereinbelow.

EXAMPLES

Example 1

The tetrapeptide H-Lys(H-Asp-NH$_2$)-Ala-Glu-NH$_2$ was found to be able to stimulate the growth of S. epidermidis on agar plates in an in-vitro hole plate assay. To this effect, an S. epidermidis growth simulation assay was employed, using potassium tellurite as the growth indicator, observed in the assay as brown zones. An S. epidermidis log phase culture at 1:200 (containing approximately $1 \times 10^7$ cfu/ml of bacteria) was used as the working culture in the experiment.

The working culture was plated onto tellurite-TSA, after which 5 mm diameter holes were respectively punched into the agar for forming the testing wells. 40 µl of a solution containing the tetrapeptide at a concentration of 1 mg/ml were then added to a first and second well, and the same volume of water was added as the control to a third well. The Petri dish was then incubated at 35° C. for 24 h.

Figure 1A:
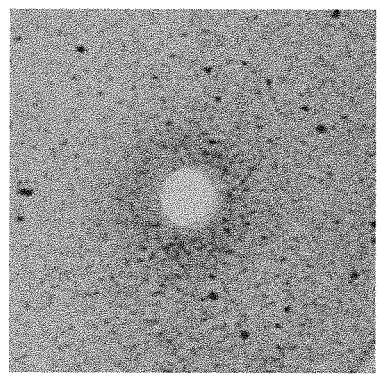
FIG. 1a shows results from the in-vitro-hole/well plate assay according to Example 1, wherein the stimulation of the growth of *S. epdermidis* having been treated with the tetrapeptide H-Lys(H-Asp-NH$_2$)-Ala-Glu-NH$_2$ may be observed in view of the formation of a black ring around the well.
Figure 1B:
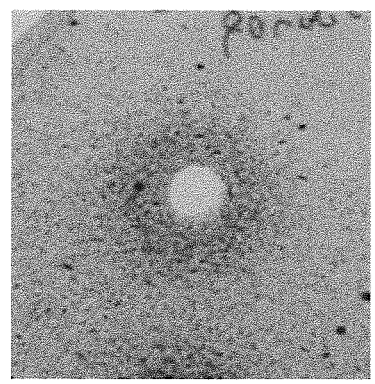
FIG. 1b shows results from the in-vitro-hole/well plate assay according to Example 1, wherein the stimulation of the growth of *S. epdermidis* having been treated with the tetrapeptide H-Lys(H-Asp-NH$_2$)-Ala-Glu-NH$_2$ may be observed in view of the formation of a black ring around the well.
Figure 1C:
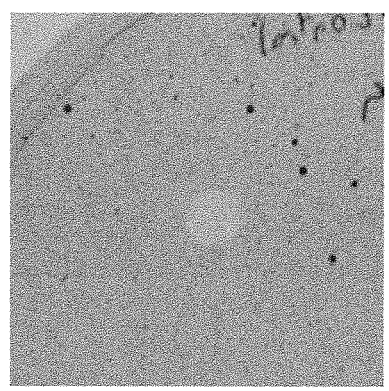
FIG. 1c shows the result from the control assay in Example 1 containing water.

The results of the assay are displayed in FIGS. 1 and 2, which respectively show the S. epidermidis culture treated with the tetrapeptide (FIGS. 1a and 1b) and the control assay with water (FIG. 1c). In particular, it is apparent from the assays containing the inventive tetrapeptide that the growth of S. epidermidis is clearly stimulated.

Example 2

A Microtiter plate having wells with a respective volume of 200 µl was used for the S. epidermidis in vitro liquid assay. To this effect, a 24 h cell culture of S. epidermidis was diluted 1:200 thus affording an optical density $OD_{600nm}$ of 0.06 in SCD-bouillon (1:2). The samples used in the experiment further contained the inventive tetrapeptide H-Lys(H-Asp-NH$_2$)-Ala-Glu-NH$_2$ in respective concentrations of 1 mg/ml and 0.2 mg/ml. As control assay, samples containing 1 mg/ml of a mixture containing Alanine, Glutamine, Lysine, and Asparagine in equal parts and samples containing no further components in addition to S. epidermidis were respectively employed. The pH of all of the samples was 6.5.

Figure 2A:
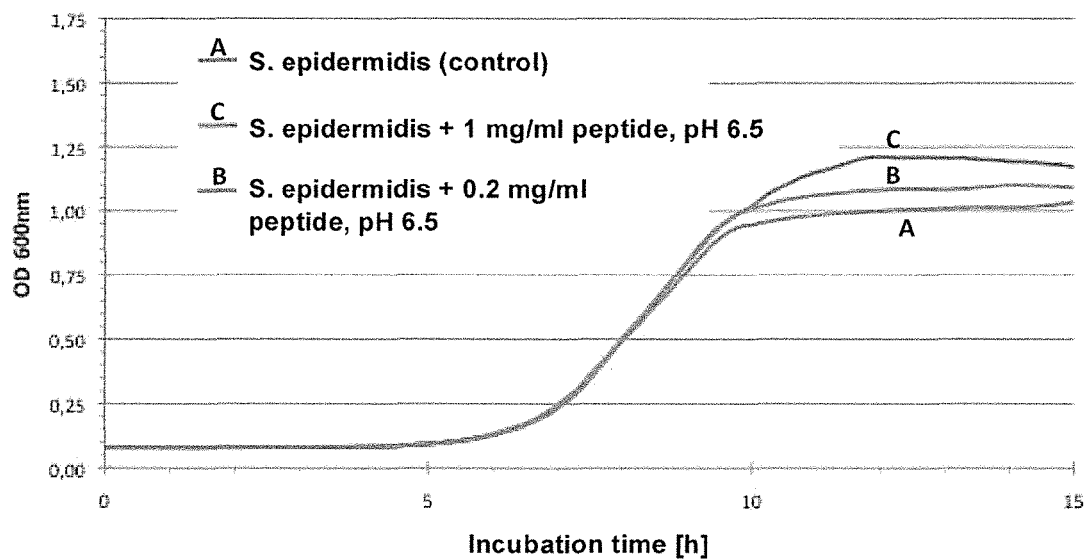
FIG. 2a shows results from the bioassay according to Example 2, displaying the stimulation of the growth of *S. epidermidis* having been treated with the tetrapeptide H-Lys(H-Asp-NH$_2$)-Ala-Glu-NH$_2$, wherein the y-axis represents the optical density $OD_{600nm}$ measured for the respective samples and the x-axis represents the incubation time in hours. Line A shows the results for the untreated sample (control), line B shows the results for the sample treated with 0.2 mg/ml of the inventive tetrapeptide, and line C shows the results for the sample treated with 1 mg/ml of the inventive tetrapeptide.
Figure 2B:
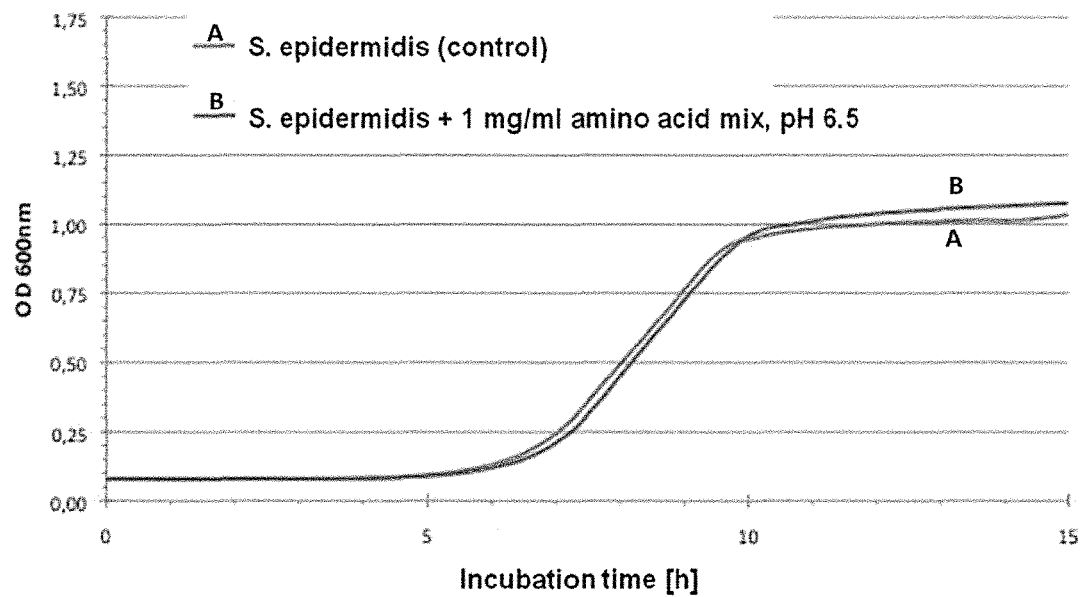
FIG. 2b shows results from the bioassay according to Example 2, displaying the influence of an mixture of four amino acids on the growth of S. epidermidis, wherein the y-axis represents the optical density $OD_{600nm}$, measured for the respective samples and the x-axis represents the incubation time in hours. Line A shows the results for the untreated sample (control) and line B shows the results for the sample treated with a mixture of Alanine, Glutamine, Lysine, and Asparagine in equal parts ("amino acid mix") at a total concentration of 1 mg/ml in the sample.

Results from the bioassay are shown in FIGS. 2a and 2b. In particular, as may be taken from FIG. 2a, the samples containing the inventive tetrapeptide (see lines B and C) clearly stimulates the growth of S. epidermidis compared to the control sample devoid of an additive (see line A), wherein the stimulation is already apparent at a concentration of 0.2 mg/ml (see line B). In particular, as may be taken from the results displayed in FIG. 2b for the sample of S. epidermidis containing a mixture of 4 amino acids (see line B), the same effect may not be observed for the constituent amino acid residues of the inventive tetrapeptide by themselves, said sample showing a progression of the S. epidermis population which is comparable to the control sample devoid of an additive (see line A).

Example 3

An S. aureus in vitro liquid assay was performed on a Microtiter plate having wells with a respective volume of 200 µl. To this effect, a 24 h cell culture of S. aureus was diluted 1:500 thus affording an optical density $OD_{600nm}$ of 0.05 in SCD-bouillon (1:2). One of the samples used in the experiment further contained the inventive tetrapeptide H-Lys(H-Asp-NH$_2$)-Ala-Glu-NH$_2$ in a concentration of 1 mg/ml. The pH of the samples was 6.5.

Figure 3:
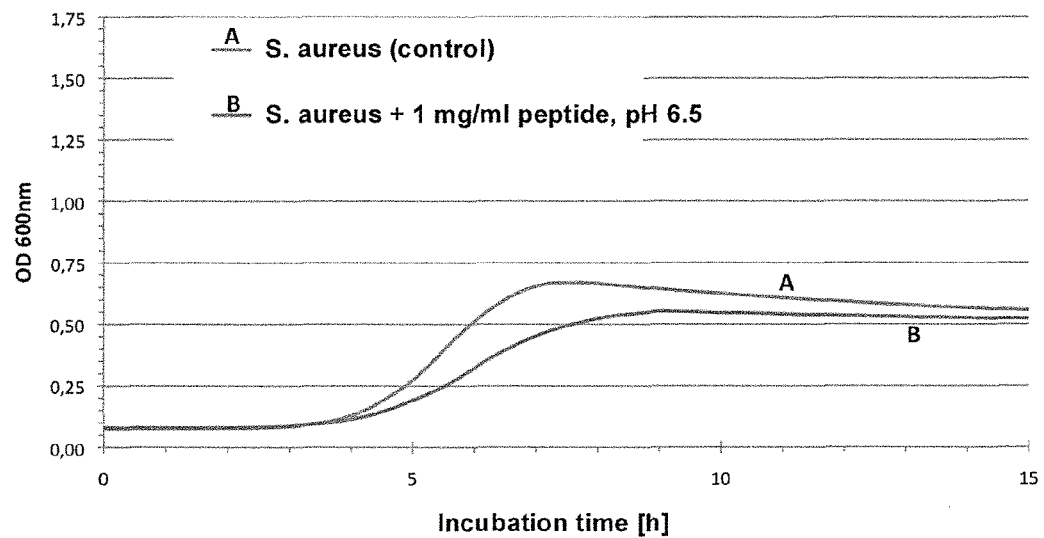
FIG. 3 shows results from the bioassay according to Example 3, displaying the inhibition of the growth of S. aureus having been treated with the tetrapeptide H-Lys(H-Asp-NH$_2$)-Ala-Glu-NH$_2$, wherein the y-axis represents the optical density $OD_{600nm}$ measured for the respective samples and the x-axis represents the incubation time in hours. Line A shows the results for the untreated sample (control), and line B shows the results for the sample treated with 1 mg/ml of the inventive tetrapeptide.

The results from the bioassay of Example 3 are shown in FIG. 3, wherein it is apparent that the growth of S. aureus was clearly inhibited in the sample containing the inventive tetrapeptide (see line B) compared the control sample devoid of an additive (see line A).

Example 4

Monolayer cultures of normal human epidermal keratinocytes (NHEK) were cultivated for a 48 h-period consisting in a 24 h pre-treatment followed by a 24 h treatment with or without Lactobacillus DSM 17250 (200 µg/ml) producing a peptide according to the present invention.

At the end of the incubation, the effect of the Lactobacillus producing a peptide according to the present invention on the secretion of pro-inflammatory cytokine IL-1α was evaluated by quantification using a commercially available ELISA kit.

The different culture conditions are summarized in Table 1.

TABLE 1

Table 1: Culture protocol and properties evaluated; LPS: Lipopolysaccharides

| | Pre-treatment | Treatment | Property evaluated |
|---|---|---|---|
| 1 | None (culture medium alone) | None (culture medium alone) | Untreated control (negative control) |
| 2 | Lactobacillus DSM 17250 | None (culture medium alone) | Pro-inflammatory effect of Lactobacillus DSM 17250 |
| 3 | LPS | None (culture medium alone) | Pro-inflammatory effect of LPS (positive control) |
| 4 | Lactobacillus DSM 17250 | LPS | Precautionary anti-inflammatory effect of Lactobacillus DSM 17250 |
| 5 | Lactobacillus DSM 17250 + LPS | Lactobacillus DSM 17250 | Protective anti-inflammatory effect of Lactobacillus DSM 17250 |

Figure 4:
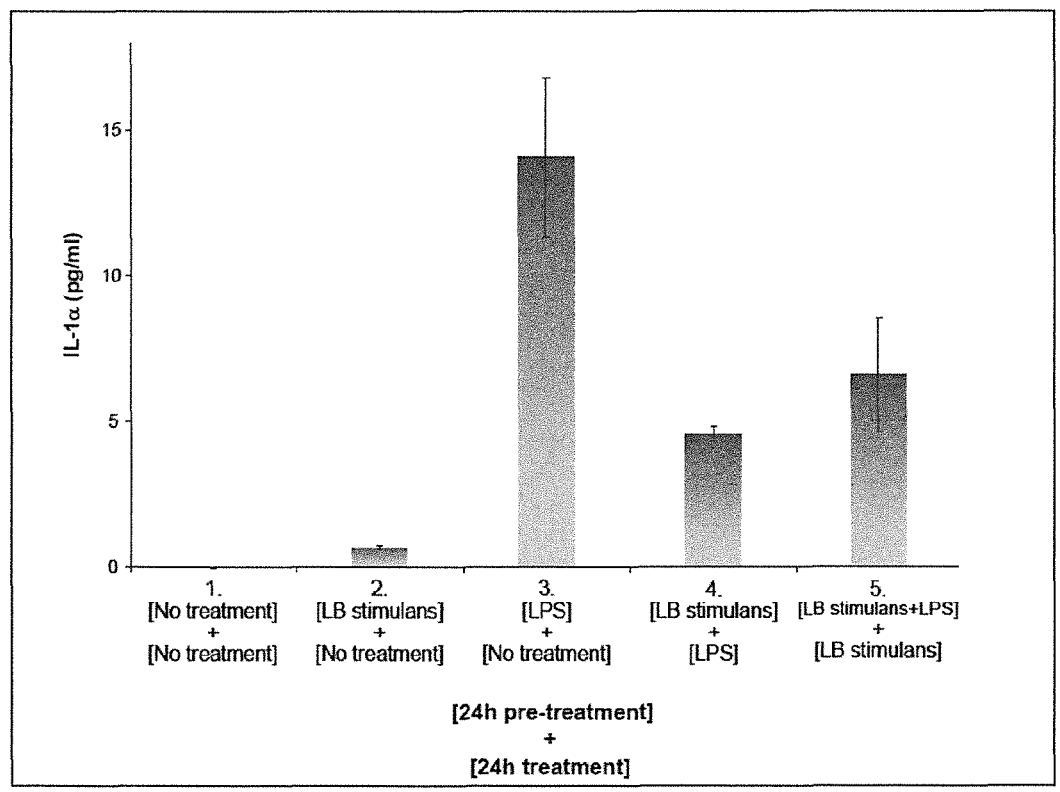
FIG. 4 shows results from the bioassay of Example 4, displaying the secretion of IL-1alpha by NHEK after 24 h of pre-treatment and 24 h of treatment. 1. Is the negative control, 2. and 3. show the pro-inflammatory effects of Lactobacillus DSM 17250 and LPS, respectively, 4. the precautionary anti-inflammatory effect of Lactobacillus DSM 17250, and 5. the protective anti-inflammatory effect of Lactobacillus DSM 17250.

The results from the determination of IL-1α in the bioassay are shown in FIG. 4. It can be concluded from the results that untreated keratinocytes do not secrete pro-inflammatory IL-1α (1, negative control) while LPS-treated keratinocytes secrete large quantities of IL-1α (3, positive control).

The cells which were pretreated with *Lactobacillus* DSM 17250 do not secrete IL-1α. Therefore, it can be concluded that the *lactobacillus* has no pro-inflammatory effect (2).

Pre-treatment with *Lactobacillus* DSM 17250 dramatically reduces IL-1α production after treatment with LPS (4). Therefore, a precautionary anti-inflammatory effect of *Lactobacillus* DSM 17250 can be concluded.

The addition of *Lactobacillus* DSM 17250 to LPS as pretreatment before treatment with the *lactobacillus* reduces the inflammatory effect of LPS. Therefore, a protective anti-inflammatory effect by the *lactobacillus* can also be concluded (5).

CITED PRIOR ART DOCUMENTS

WO 2006/136420 A2
WO 2005/048968 A1
WO 00/43417 A1
U.S. Pat. No. 6,620,419 B1
U.S. Pat. No. 6,492,326 B1
Rollan et al., Int. J. Food Microbiol. 70 (2001), 303-307
Matsuquchi et al., Clin. Diagn. Lab. Immunol. 10 (2003), 259-266
Stentz et al., Appl. Environ. Microbiol. 66 (2000), 4272-4278
Varmanen et al., J. Bacteriology 182 (2000), 146-154
Schrader, Grundlagen and Rezepturen der Kosmetika, Hüthig Buch Verlag, Heidelberg, $2^{nd}$ edition, 1989, $3^{rd}$ part

The invention claimed is:

1. A peptide of the following formula (III):

Lys(H-Asp-$R^2$)-Ala-Glu    (III)

or a salt thereof;
wherein $R^2$ is OH or $NH_2$;
wherein the C-terminal carboxyl group in Glu is optionally an amide Glu-$NR^3R^4$, and $R^3$ and $R^4$ are independently from one another H or alkyl;
and wherein the N-terminal amino group in Lys is optionally $NR^5R^6$, and $R^5$ and $R^6$ are independently from one another H or alkyl.

2. The peptide of claim 1, wherein $R^3$ and $R^4$ are independently H or (C1-C3)alkyl.

3. The peptide of claim 1, wherein $R^3$ and $R^4$ are H.

4. The peptide of claim 1, wherein $R^5$ and $R^6$ are independently H or (C1-C3)alkyl.

5. The peptide of claim 1, wherein $R^5$ and $R^6$ are H.

6. The peptide of claim 1, wherein said peptide is contained in a cleansing agent for application to the epidermis, wherein the cleansing agent is a soap or lotion.

7. The peptide of claim 6, wherein the cleansing agent is contained in or applied as an aerosol.

8. The peptide of claim 1, wherein said peptide is contained in a cleansing agent for application to the scalp, wherein the cleansing agent is a shampoo.

9. The peptide of claim 1, wherein said peptide is contained in a cleansing agent for application to the facial skin, wherein the cleansing agent is a soap or lotion.

10. The peptide of claim 1, wherein said peptide is contained in a formulation for application to the epidermis, wherein the formulation is a liquid or semisolid solution, lotion, cream, gel, or ointment.

11. The peptide of claim 10, wherein the formulation is contained in or applied as an aerosol.

12. The peptide of claim 1, wherein said peptide is contained in a formulation for application to the scalp, wherein the formulation is a liquid or semisolid solution, lotion, cream, gel, or ointment.

13. The peptide of claim 1, wherein said peptide is contained in a formulation for application to the facial skin, wherein the formulation is a liquid or semisolid solution, lotion, cream, gel, or ointment.

14. A cosmetic composition comprising a peptide according to claim 1.

15. The cosmetic composition of claim 14, wherein said composition comprises the peptide in a concentration of from 0.005 to 20 mg/ml.

16. The cosmetic composition of claim 14, wherein said composition comprises the peptide in a concentration of from 0.01 to 10 mg/ml.

17. The cosmetic composition of claim 14, wherein said composition comprises the peptide in a concentration of from 0.05 to 5 mg/ml.

18. The cosmetic composition of claim 14, wherein said composition comprises the peptide in a concentration of from 0.1 to 2 mg/ml.

19. The cosmetic composition of claim 14, wherein said composition comprises the peptide in a concentration of from 0.2 to 1 mg/ml.

20. The composition of claim 14, wherein said composition further comprises one or more cosmetically acceptable carriers or excipients.

21. The composition of claim 14, wherein said composition is contained in a cleansing agent for application to the epidermis, wherein the cleansing agent is a soap or lotion.

22. The composition of claim 14, wherein said composition is contained in a cleansing agent for application to the scalp, wherein the cleansing agent is a shampoo.

23. The composition of claim 14, wherein said composition is contained in a cleansing agent for application to the facial skin, wherein the cleansing agent is a facial lotion.

24. The composition of claim 14, wherein said composition is contained in a formulation for application to the epidermis, wherein the formulation is a liquid or semisolid solution, lotion, cream, gel, or ointment.

25. The composition of claim 14, wherein said composition is contained in a formulation for application to the scalp, wherein the formulation is a liquid or semisolid solution, lotion, cream, gel, or ointment.

26. The composition of claim 14, wherein said composition is contained in a formulation for application to the facial skin, wherein the formulation is a liquid or semisolid solution, lotion, cream, gel, or ointment.

27. A pharmaceutical composition comprising a peptide according to claim 1.

28. The pharmaceutical composition of claim 27, wherein said composition comprises the peptide in a concentration of from 0.01 to 100 mg/ml.

29. The pharmaceutical composition of claim 27, wherein said composition comprises the peptide in a concentration of from 0.05 to 50 mg/ml.

30. The pharmaceutical composition of claim 27, wherein said composition comprises the peptide in a concentration of from 0.1 to 10 mg/ml.

31. The pharmaceutical composition of claim 27, wherein said composition comprises the peptide in a concentration of from 0.2 to 5 mg/ml.

32. The pharmaceutical composition of claim 27, wherein said composition comprises the peptide in a concentration of from 0.5 to 2 mg/ml.

33. The composition of claim 27, wherein said composition further comprises one or more pharmaceutically acceptable carriers or excipients.

* * * * *